US008828438B2

(12) United States Patent
Friesen et al.

(10) Patent No.: US 8,828,438 B2
(45) Date of Patent: *Sep. 9, 2014

(54) PHARMACEUTICAL COMPOSITIONS OF CHOLESTERYL ESTER TRANSFER PROTEIN INHIBITORS AND HMG-COA REDUCTASE

(75) Inventors: Dwayne Thomas Friesen, Bend, OR (US); Bruno Caspar Hancock, North Stonington, CT (US); Rodney James Ketner, Bend, OR (US); David Keith Lyon, Bend, OR (US); James Alan Shriver Nightingale, Bend, OR (US); Ravi Mysore Shanker, Stonington, CT (US)

(73) Assignee: Bend Research, Inc., Bend, OR (US)

( * ) Notice: Subject to any disclaimer, the term of this patent is extended or adjusted under 35 U.S.C. 154(b) by 1476 days.

This patent is subject to a terminal disclaimer.

(21) Appl. No.: 11/920,473

(22) PCT Filed: May 22, 2006

(86) PCT No.: PCT/IB2006/001407
§ 371 (c)(1),
(2), (4) Date: Nov. 14, 2007

(87) PCT Pub. No.: WO2006/129167
PCT Pub. Date: Dec. 7, 2006

(65) Prior Publication Data
US 2009/0118328 A1  May 7, 2009

Related U.S. Application Data

(60) Provisional application No. 60/686,109, filed on May 31, 2005.

(51) Int. Cl.
*A61K 31/4706* (2006.01)
*A61K 47/38* (2006.01)
*A61K 31/41* (2006.01)
*A61K 31/40* (2006.01)
*A61K 47/32* (2006.01)
*A61K 45/06* (2006.01)
*A61K 9/16* (2006.01)

(52) U.S. Cl.
CPC ............... *A61K 45/06* (2013.01); *A61K 9/1611* (2013.01); *A61K 9/1635* (2013.01); *A61K 31/40* (2013.01); *A61K 31/4706* (2013.01); *A61K 9/1652* (2013.01)
USPC ........... 424/486; 514/313; 514/381; 514/781; 514/772

(58) Field of Classification Search
None
See application file for complete search history.

(56) References Cited

FOREIGN PATENT DOCUMENTS

| EP | 1027888 | * | 8/2000 |
|---|---|---|---|
| WO | WO 2004/056358 A | | 7/2004 |
| WO | WO 2004/056359 A | | 7/2004 |
| WO | WO 2004 056395 | * | 7/2004 |
| WO | WO 2004/056395 A | | 7/2004 |

* cited by examiner

*Primary Examiner* — Suzanne Ziska
*Assistant Examiner* — Thurman Wheeler
(74) *Attorney, Agent, or Firm* — Klarquist Sparkman, LLP

(57) ABSTRACT

A solid amorphous dispersion comprises a cholesteryl ester transfer protein (CETP) inhibitor, an inhibitor of 3-hydroxy-3-methylglutaryl-coenzyme A reductase (HMG-CoA reductase inhibitor), and a concentration enhancing polymer. At least a major portion of the CETP inhibitor in the dispersion is amorphous. The solid amorphous dispersion provides concentration-enhancement of the CETP inhibitor when administered to an aqueous use environment.

9 Claims, No Drawings

PHARMACEUTICAL COMPOSITIONS OF CHOLESTERYL ESTER TRANSFER PROTEIN INHIBITORS AND HMG-COA REDUCTASE

CROSS-REFERENCE TO RELATED APPLICATIONS

This is a 371 of PCT/IB2006/001407 filed 22 May 2006 and claims priority of U.S. Ser. No. 60/686,109 filed 31 May 2005.

BACKGROUND

It is known that combination therapy of a cholesteryl ester transfer protein (CETP) inhibitor and inhibitors of 3-hydroxy-3-methylglutaryl-coenzyme A reductase (HMG-CoA reductase inhibitors) may be used to treat elevated low-density lipoprotein (LDL) cholesterol and low high-density lipoprotein (HDL) cholesterol levels. For example, WO02/13797 A2 relates to pharmaceutical combinations of cholesteryl ester transfer protein inhibitors and atorvastatin. The application discloses that the compounds may be generally administered separately or together, with a pharmaceutically acceptable carrier, vehicle or diluent. The compounds may be administered individually or together in any conventional oral, parenteral or transdermal dosage form. For oral administration, the dosage form may take the form of solutions, suspensions, tablets, pills, capsules, powders and the like.

CETP inhibitors, particularly those that have high binding activity, are generally hydrophobic, have extremely low aqueous solubility and have low oral bioavailability when dosed conventionally. Such compounds have generally proven to be difficult to formulate for oral administration such that high bioavailabilities are achieved. Accordingly, CETP inhibitors must be formulated so as to be capable of providing good bioavailability. Such formulations are generally termed "solubility-improved" forms. One method for increasing the bioavailability of a CETP inhibitor is to form a solid amorphous dispersion of the drug and a concentration-enhancing polymer. See, e.g., commonly assigned, copending U.S. Patent Application Publication No. 2002/0103225 A1 and U.S. Patent Application Publication No. 2003/0186952 A1, the disclosures of which are incorporated herein by reference.

However, while it is desired to combine the CETP inhibitor and an HMG-CoA reductase inhibitor into a single dosage form, combining a CETP inhibitor in a solubility-improved form and an HMG-CoA reductase inhibitor into a single dosage form presents a number of potential problems. Some HMG-CoA reductase inhibitor compounds are unstable in that they are susceptible to heat, moisture, low pH environment, and light. Some HMG-CoA reductase inhibitors, such as atorvastatin, pravastatin, florastatin, and rosuvastatin, are in the form of hydroxy acids that will degrade to a lactone in an acidic environment. Other HMG-CoA-reductase inhibitors, such as lovastatin and simvastatin, contain substituents that readily degrade in an acidic environment. When packaged in the form of tablets, powders, granules, or within capsules, the HMG-CoA reductase inhibitor may be further destabilized by contact with the molecular moieties of other components of the dosage form. Since pharmaceutical dosage form components such as binders, diluents, surfactants and the like may adversely interact with the active ingredient compound, a stabilizing means may be required for effective pharmaceutical dosages. For example, U.S. Pat. No. 6,126,971 discloses the addition of a stabilizing agent such as calcium carbonate to stabilize the HMG-CoA reductase inhibitor atorvastatin calcium. Nevertheless, the means for stabilizing the HMG-CoA reductase inhibitor must also allow solubilization of the CETP inhibitor.

Thus, there is a continuing need for a dosage form containing a CETP inhibitor and an HMG-CoA reductase inhibitor that stabilizes the HMG-CoA reductase inhibitor and that provides good bioavailability for the CETP inhibitor.

SUMMARY OF THE INVENTION

The invention provides a solid amorphous dispersion comprising (1) a CETP inhibitor, (2) an acid sensitive HMG-CoA reductase inhibitor, and (3) a concentration-enhancing polymer selected from the group consisting of neutral polymers, neutralized acidic polymers, and mixtures thereof. At least a major portion of the CETP inhibitor in the dispersion is amorphous. The solid amorphous dispersion provides concentration-enhancement of the CETP inhibitor when administered to an aqueous use environment, while providing chemical stability of the HMG-CoA reductase inhibitor.

The present invention simultaneously solves several problems attendant to co-dosing a CETP inhibitor and an HMG-CoA reductase inhibitor. The bioavailability of CETP inhibitors may be substantially improved by forming a solid amorphous dispersion of the CETP inhibitor and a concentration-enhancing polymer. However, when an HMG-CoA reductase inhibitor is included in the solid amorphous dispersion along with the CETP inhibitor and certain concentration-enhancing polymers, the inventors observed chemical degradation of the HMG-CoA reductase inhibitor. The inventors solved the chemical degradation problem by selecting concentration-enhancing polymers for the solid amorphous dispersion that result in improved chemical stability for the HMG-CoA reductase inhibitor, while providing enhanced bioavailability of the CETP inhibitor. Specifically, the concentration-enhancing polymer should be selected from neutral polymers, neutralized acidic polymers, and mixtures thereof.

In addition, HMG-CoA reductase inhibitors, such as atorvastatin calcium, are characterized by a relatively low daily dose (typically 1 to 80 mg/d) and by a small crystal size. This can result in content uniformity issues. Such issues can be further exacerbated by the combination of two active ingredients. Because the HMG-CoA reductase inhibitor and CETP inhibitor are both uniformly distributed in the solid amorphous dispersion, no mixing of separate compositions is required. As a result, dosage forms made using the solid amorphous dispersion will have improved content uniformity than dosage forms based on two compositions—one containing the HMG-CoA reductase inhibitor and one containing the CETP inhibitor.

Reference to a "use environment" can either mean in vivo fluids, such as the GI tract, subdermal, intranasal, buccal, intrathecal, ocular, intraaural, subcutaneous spaces, vaginal tract, arterial and venous blood vessels, pulmonary tract or intramuscular tissue of an animal, such as a mammal and particularly a human, or the in vitro environment of a test solution, such as phosphate buffered saline (PBS) or a Model Fasted Duodenal (MFD) solution. An appropriate PBS solution is an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. An appropriate MFD solution is the same PBS solution wherein additionally is present 7.3 mM sodium taurocholic acid and 1.4 mM of 1-palmitoyl-2-oleyl-sn-glycero-3-phosphocholine.

"Administration" to a use environment means, where the in vivo use environment is the GI tract, delivery by ingestion or swallowing or other such means to deliver the drugs. One skilled in the art will understand that "administration" to other in vivo use environments means contacting the use environment with the composition of the invention using methods known in the art. See for example, Remington: The Science and Practice of Pharmacy, 20$^{th}$ Edition (2000). Where the use environment is in vitro, "administration" refers to placement or delivery of the dosage form to the in vitro test medium. Where release of drug into the stomach is not desired but release of the drug in the duodenum or small intestine is desired, the use environment may also be the duodenum or small intestine. In such cases, "introduction" to a use environment is that point in time when the dosage form leaves the stomach and enters the duodenum.

The foregoing and other objectives, features, and advantages of the invention will be more readily understood upon consideration of the following detailed description of the invention.

DETAILED DESCRIPTION OF THE INVENTION

The present invention provides a solid amorphous dispersion comprising (1) a CETP inhibitor, (2) an HMG-CoA reductase inhibitor, and (3) a concentration-enhancing polymer, wherein at least a major portion of the CETP inhibitor in the dispersion is amorphous. CETP inhibitors, HMG-CoA reductase inhibitors, concentration-enhancing polymers, and methods for forming the solid amorphous dispersion are discussed in more detail below.

Cholesteryl Ester Transfer Protein Inhibitors

The CETP inhibitor may be any compound capable of inhibiting the cholesteryl ester transfer protein. Solid amorphous dispersions are particularly useful for CETP inhibitors that have sufficiently low aqueous solubility, low bioavailability or slow rate of absorption such that it is desirable to increase their concentration in an aqueous environment of use. The CETP inhibitor is typically "sparingly water-soluble," which means that the CETP inhibitor has a minimum aqueous solubility of less than about 1 to 2 mg/mL at any physiologically relevant pH (e.g., pH 1-8) and at about 22° C. Many CETP inhibitors are "substantially water-insoluble," which means that the CETP inhibitor has a minimum aqueous solubility of less than about 0.01 mg/mL (or 10 µg/ml) at any physiologically relevant pH (e.g., pH 1-8) and at about 22° C. (Unless otherwise specified, reference to aqueous solubility herein and in the claims is determined at about 22° C.) Compositions of the present invention find greater utility as the solubility of the CETP inhibitors decreases, and thus are preferred for CETP inhibitors with solubilities less than about 10 µg/mL, more preferred for CETP inhibitors with solubilities less than about 2 µg/mL, and even more preferred for CETP inhibitors with solubilities less than about 1 µg/mL. Many CETP inhibitors have even lower solubilities (some even less than about 0.1 µg/mL), and require dramatic concentration enhancement to be sufficiently bioavailable upon oral dosing for effective plasma concentrations to be reached at practical doses. Alternatively, the CETP inhibitor has a minimum aqueous solubility over the pH range of 6.5 to 7.5 of less than about 10 µg/mL, more preferably less than about 2 µg/mL, and even more preferably of less than about 1 µg/mL.

In general, the CETP inhibitor has a dose-to-aqueous solubility ratio greater than about 100 mL, where the solubility (mg/mL) is the minimum value observed in any physiologically relevant aqueous solution (e.g., those with pH values from 1 to 8) including USP simulated gastric and intestinal buffers, and dose is in mg. Compositions of the present invention, as mentioned above, find greater utility as the solubility of the CETP inhibitor decreases and the dose increases. Thus, the compositions are preferred as the dose-to-solubility ratio increases, and thus are preferred for dose-to-solubility ratios of at least about 1000 mL, and more preferred for dose-to-solubility ratios of at least about 5,000 mL, and even more preferred for dose-to-solubility ratios of at least about 10,000 mL. The dose-to-solubility ratio may be determined by dividing the dose (in mg) by the aqueous solubility (in mg/ml).

The low solubility of CETP inhibitors is primarily due to the hydrophobic nature of CETP inhibitors. Log P, defined as the base 10 logarithm of the ratio of (1) the drug concentration in an octanol phase to (2) the drug concentration in a water phase when the two phases are in equilibrium with each other, is a widely accepted measure of hydrophobicity. Log P may be measured experimentally or calculated using methods known in the art. The Log P may be estimated experimentally by determining the ratio of the drug solubility in octanol to the drug solubility in water. When using a calculated value for Log P, the highest value calculated using any generally accepted method for calculating Log P is used. Calculated Log P values are often referred to by the calculation method, such as Clog P, Alog P, and Mlog P. The Log P may also be estimated using fragmentation methods, such as Crippen's fragmentation method (J. Chem. Inf. Comput. Sci., 27, 21 (1987)); Viswanadhan's fragmentation method (J. Chem. Inf. Comput. Sci., 29, 163 (1989)); or Broto's fragmentation method (Eur. J. Med. Chem.-Chim. Theor., 19, 71 (1984). Preferably the Log P value is calculated by using the average value estimated using Crippen's, Viswanadhan's, and Broto's fragmentation methods. In general, Log P values for CETP inhibitors are greater than about 4 and are often greater than about 5.

The compositions of the present invention are also suitable for CETP inhibitors that have low melting points. In one embodiment, the CETP inhibitor has a melting point of about 150° C. or less, and preferably about 140° C. or less.

Primarily, as a consequence of some or all of these properties, CETP inhibitors typically have very low absolute bioavailabilities. Preferably, the absolute bioavailability of the CETP inhibitors when dosed orally in their undispersed state is less than about 10% and more often less than about 5%.

In the following, by "pharmaceutically acceptable forms" thereof is meant any pharmaceutically acceptable derivative or variation, including stereoisomers, stereoisomer mixtures, enantiomers, solvates, hydrates, isomorphs, polymorphs, salt forms and prodrugs.

Specific examples of CETP inhibitors include [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib), [2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R,4S]4-[(3,5-Bis-trifluoromethyl-benzyl)-methoxycarbonyl-amino]-2-ethyl-6-trifluoromethyl-3,4-dihydro-2H-quinoline-1-carboxylic acid isopropyl ester, (2R)-3-[[3-(4-chloro-3-ethylphenoxy)phenyl][[3-(1,1,2,2-tetrafluoroethoxy)phenyl]methyl]amino]-1,1,1-trifluoro-2-propanol, (2R,4R,4S)-4-[amino-(3,5-bis-(trifluoromethyl-phenyl)-methyl]-2-ethyl-6-(trifluoromethyl)-3,4-dihydroquinoline-1-carboxylic acid isopropyl ester, S-[2-([[1-(2-ethylbutyl)cyclohexyl]carbonyl]amino)phenyl]2-methylpropanethioate, trans-4-[[[2-[[[3,5-bis (trifluoromethyl)phenyl]methyl](2-methyl-2H-tetrazol-5-yl)amino]methyl]-4-(trifluoromethyl)phenyl]ethylamino]methyl]-cyclohexaneacetic acid, trans-4-[[[2-[[[[3,5-bis(trifluoromethyl)phenyl]methyl](2-methyl-2H-tetrazol-5-yl)amino]methyl]-5-methyl-4-(trifluoromethyl)phenyl]ethylamino]methyl]-cyclohexaneacetic acid, the drugs disclosed in the drugs disclosed in commonly owned U.S. patent application Ser. Nos. 09/918,127 and 10/066,091, the disclosures of both of which are incorporated herein by reference, and the drugs disclosed in the following patents and published applications, the disclosures of all of which are incorporated herein by reference: DE 19741400 A1; DE 19741399 A1; WO 9914215 A1; WO 9914174; DE 19709125 A1; DE 19704244 A1; DE 19704243 A1; EP 818448 A1; WO 9804528 A2; DE 19627431 A1; DE 19627430 A1; DE 19627419 A1; EP 796846 A1; DE 19832159; DE 818197; DE 19741051; WO 9941237 A1; WO 9914204 A1; WO 9835937 A1; JP 11049743; WO 200018721; WO 200018723; WO 200018724; WO 200017164; WO 200017165; WO 200017166; WO 2004020393; EP 992496; and EP 987251.

In a preferred embodiment, the CETP inhibitor is [2R,4S]-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester also known as torcetrapib. Torcetrapib is shown by the following Formula

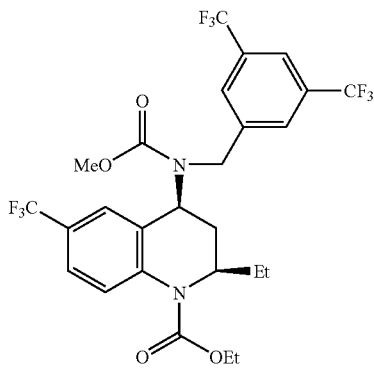 [SMILES: CCOC(=O)N1c2ccc(C(F)(F)F)cc2[C@@H](N(Cc2cc(C(F)(F)F)cc(C(F)(F)F)c2)C(=O)OC)C[C@H]1CC]

CETP inhibitors, in particular torcetrapib, and methods for preparing such compounds are disclosed in detail in U.S. Pat. Nos. 6,197,786 and 6,313,142, in PCT Application Nos. WO 01/40190A1, WO 02/088085A2, and WO 02/088069A2, the disclosures of which are herein incorporated by reference. Torcetrapib has an unusually low solubility in aqueous environments such as the lumenal fluid of the human GI tract. The aqueous solubility of torcetrapib is less than about 0.04 µg/ml. Torcetrapib must be presented to the GI tract in a solubility-enhanced form in order to achieve a sufficient drug concentration in the GI tract in order to achieve sufficient absorption into the blood to elicit the desired therapeutic effect.

HMG-CoA Reductase Inhibitors

The HMG-CoA reductase inhibitor may be any HMG-CoA reductase inhibitor capable of lower plasma concentrations of low-density lipoprotein, total cholesterol, or both. The HMG-CoA reductase inhibitor is acid sensitive, meaning that the drug either chemically reacts with or otherwise degrades in the presence of acidic species, as described herein. Examples of chemical reactions include hydrolysis, lactonization, or transesterification in the presence of acidic species.

In one aspect, the HMG-CoA reductase inhibitor is from a class of therapeutics commonly called statins. Examples of HMG-CoA reductase inhibitors that may be used include but are not limited to lovastatin (MEVACOR®; see U.S. Pat. Nos. 4,231,938; 4,294,926; 4,319,039), simvastatin (ZOCOR®; see U.S. Pat. Nos. 4,444,784; 4,450,171; 4,820,850; 4,916,239), pravastatin (PRAVACHOL®; see U.S. Pat. Nos. 4,346,227; 4,537,859; 4,410,629; 5,030,447 and 5,180,589), lactones of pravastatin (see U.S. Pat. No. 4,448,979), fluvastatin (LESCOL®; see U.S. Pat. Nos. 5,354,772; 4,911,165; 4,739,073; 4,929,437; 5,189,164; 5,118,853; 5,290,946; 5,356,896), lactones of fluvastatin, atorvastatin (LIPITOR®; see U.S. Pat. Nos. 5,273,995; 4,681,893; 5,489,691; 5,342,952), lactones of atorvastatin, rosuvastatin (Crestor®; see U.S. Pat. No. 5,260,440 and RE37314, and European Patent No. EP521471), lactones of rosuvastatin, itavastatin, nisvastatin, visastatin, atavastatin, bervastatin, compactin, dihydrocompactin, dalvastatin, fluindostatin, pitavastatin, mevastatin (see U.S. Pat. No. 3,983,140), and velostatin (also referred to as synvinolin). Other examples of HMG-CoA reductase inhibitors are described in U.S. Pat. Nos. 5,217,992; 5,196,440; 5,189,180; 5,166,364; 5,157,134; 5,110,940; 5,106,992; 5,099,035; 5,081,136; 5,049,696; 5,049,577; 5,025,017; 5,011,947; 5,010,105; 4,970,221; 4,940,800; 4,866,058; 4,686,237; 4,647,576; European Application Nos. 0142146A2 and 0221025A1; and PCT Application Nos. WO 86/03488 and WO 86/07054. Also included are pharmaceutically acceptable forms of the above. All of the above references are incorporated herein by reference. Preferably the HMG-CoA reductase inhibitor is selected from the group consisting of fluvastatin, lovastatin, pravastatin, atorvastatin, simvastatin, rivastatin, mevastatin, velostatin, compactin, dalvastatin, fluindostatin, rosuvastatin, pitavastatin, dihydrocompactin, and pharmaceutically acceptable forms thereof. By "pharmaceutically acceptable forms" is meant any pharmaceutically acceptable derivative or variation, including stereoisomers, stereoisomer mixtures, enantiomers, solvates, hydrates, isomorphs, polymorphs, salt forms and prodrugs.

A test to determine whether an HMG-CoA reductase inhibitor is acid sensitive is to administer the drug to an acidic aqueous solution and plot drug concentration versus time. The acidic aqueous solution should have a pH of from 1-4 and be at a temperature of about 40° C. HMG-CoA reductase inhibitors that are acid sensitive are those for which the drug concentration decreases by at least 1% within 24 hours of administration of the drug to the acidic solution. If the drug concentration changes by 1% in the 6-24 hour time period, then the drug is "slightly acid-sensitive." If the drug concentration changes by 1% in the 1-6 hour time period, then the drug is "moderately acid-sensitive." If the drug concentration changes by 1% in less than 1 hour, then the drug is "highly acid-sensitive." The present invention finds increasing utility for HMG-CoA reductase inhibitors that are slightly acid-sensitive, moderately acid-sensitive and highly acid-sensitive.

In one embodiment, the HMG-CoA reductase inhibitor is selected from the group consisting of trans-6-[2-(3 or 4-carboxamido-substituted pyrrol-1-yl)alkyl]-4-hydroxypyran-2-ones and corresponding pyran ring-opened hydroxy acids derived therefrom. These compounds have been described in U.S. Pat. No. 4,681,893, incorporated herein by reference.

One preferred HMG-CoA reductase inhibitor is atorvastatin trihydrate hemi-calcium salt. This preferred compound is the ring-opened form of (2R-trans)-5-(4-fluorophenyl)-2-(1 methylethyl)-N,4-diphenyl-1-[2-(tetrahydro-4-hydroxy-6-oxo-2H-pyran-2-yl)ethyl]-1H-pyrrole-3-carboxamide, namely, the enantiomer [R—(R*,R*)]-2-(4-fluorophenyl-β, δ-dihydroxy-5-(1-methylethyl)-3-phenyl-4-[(phenylamino) carbonyl)]-1H-pyrrole-1-heptanoic acid hemicalcium salt. Its chemical structure may be represented by the following structure:

Formula A

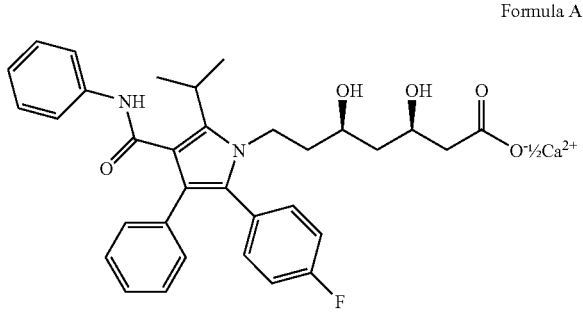

The specific isomer has been described in U.S. Pat. No. 5,273,995, herein incorporated by reference. In a preferred embodiment, the HMG-CoA reductase inhibitor is selected from the group consisting of atorvastatin, the cyclized lactone form of atorvastatin, a 2-hydroxy, 3-hydroxy or 4-hydroxy derivative of such compounds, and pharmaceutically acceptable forms thereof.

In practice, use of the salt form amounts to use of the acid or lactone form. Appropriate pharmaceutically acceptable salts are those derived from bases such as sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine and the like. Preferably, the lithium, calcium, magnesium, aluminum and ferrous or ferric salts are prepared from the sodium or potassium salt by adding the appropriate reagent to a solution of the sodium or potassium salt, i.e., addition of calcium chloride to a solution of the sodium or potassium salt of the compound of the Formula A will give the calcium salt thereof.

Solid Amorphous Dispersions

The solid amorphous dispersion of the present invention comprises (1) a CETP inhibitor, (2) an acid sensitive HMG-CoA reductase inhibitor, and (3) a concentration-enhancing polymer. By solid amorphous dispersion is meant a solid material in which at least a portion of the CETP inhibitor is in the amorphous form and dispersed in the polymer. Such solid amorphous dispersions are sometimes referred to as molecular dispersions. Homogeneous solid amorphous dispersions (described below) may be referred to as solid solutions.

The solid amorphous dispersions of the present invention comprise a plurality of particles, each of the particles comprising a CETP inhibitor, an acid sensitive HMG-CoA reductase inhibitor, and a concentration-enhancing polymer. This is in contrast, for example, to a physical mixture of two or more different types of particles, such as particles of an acid sensitive HMG-CoA reductase inhibitor and particles of a solid amorphous dispersion of a CETP inhibitor in a concentration-enhancing polymer that are blended, granulated, or otherwise physically mixed. Such physical mixtures are not considered to be a solid amorphous dispersion comprising a CETP inhibitor, an acid sensitive HMG-CoA reductase inhibitor, and a concentration-enhancing polymer, and are not a part of the present invention.

As used herein, the term "amorphous" means simply that the drug is in a non-crystalline state. The term "crystalline" refers to solid material in which atoms or molecules are arranged in a definite pattern that is repeated regularly in three dimensions. The term "non-crystalline" refers to solid material that is not crystalline, and therefore does not have long-range three-dimensional translational order. As used herein, material in a non-crystalline state is referred to as being in an amorphous state. The term "amorphous" is intended to include not only material which has essentially no order, but also material which may have some small degree of order, but the order is in less than three dimensions and/or is only over short distances. Partially crystalline materials, liquid crystals, and disordered crystals are included as well. Amorphous material may be characterized by techniques known in the art such as powder x-ray diffraction (PXRD) crystallography, solid state NMR, or thermal techniques such as differential scanning calorimetry (DSC). For example, when evaluated by PXRD, amorphous material exhibits a deviation from a flat baseline, referred to in the art as an amorphous halo.

Preferably, at least a major portion of the CETP inhibitor in the solid amorphous dispersion is amorphous. As used herein, the term "a major portion" of the CETP inhibitor means that at least about 60 wt % of the CETP inhibitor in the solid amorphous dispersion is in the amorphous form, rather than the crystalline form. Preferably, the CETP inhibitor in the solid amorphous dispersion is substantially amorphous. As used herein, "substantially amorphous" means that the amount of the CETP inhibitor in amorphous form is at least about 75 wt % (that is, the amount in crystalline form does not exceed about 25 wt %). More preferably, the CETP inhibitor in the solid amorphous dispersion is "almost completely amorphous," meaning that the amount of CETP inhibitor in amorphous form is at least about 90 wt % (that is, the amount in the crystalline form does not exceed about 10 wt %). Amounts of crystalline CETP inhibitor may be measured by Powder X-Ray Diffraction (PXRD), Scanning Electron Microscope (SEM) analysis, differential scanning calorimetry (DSC), or any other standard quantitative measurement.

Preferably, the amorphous CETP inhibitor in the solid amorphous dispersion is substantially homogeneous so that the CETP inhibitor is dispersed as homogeneously as possible throughout the polymer. As used herein, "substantially homogeneous" means that the fraction of CETP inhibitor that is present in relatively pure amorphous drug domains or regions within the solid amorphous dispersion is relatively small, on the order of less than about 20 wt %, and preferably less than about 10 wt % of the total amount of CETP inhibitor. Solid amorphous dispersions in which the CETP inhibitor is substantially homogeneous generally are more physically stable and have improved concentration-enhancing properties and, in turn, improved bioavailability, relative to dispersions in which the CETP inhibitor is not substantially homogeneous.

When subjected to thermal analysis, such as by differential scanning calorimetry (DSC), it is preferred that the solid amorphous dispersion exhibit at least one glass-transition temperature (Tg) that is intermediate that of pure CETP inhibitor and pure polymer, indicating that at least a portion of the CETP inhibitor is present in the dispersion as a solid solution (sometimes referred to as a molecular dispersion) of CETP inhibitor and polymer.

The HMG-CoA reductase inhibitor may be amorphous or crystalline in the solid amorphous dispersion. In one embodiment, at least a portion of the HMG-CoA reductase inhibitor in the solid amorphous dispersion is amorphous. The amount of amorphous HMG-CoA reductase inhibitor in the solid amorphous dispersion may be at least about 10 wt %, at least about 20 wt %, at least about 30 wt %, at least about 40 wt %, at least about 50 wt %, at least about 60 wt %, at least about 70 wt %, at least about 80 wt %, or even at least about 90 wt %. In one embodiment, at least a major portion of the HMG-CoA reductase inhibitor in the solid amorphous dispersion is amorphous, meaning that at least about 60 wt % of the HMG-CoA reductase inhibitor in the solid amorphous dispersion is in the amorphous form, rather than the crystalline form. In another embodiment, the HMG-CoA reductase inhibitor in the solid amorphous dispersion is substantially amorphous, meaning that the amount of HMG-CoA reductase inhibitor in amorphous form is at least about 75 wt % (that is, the amount in crystalline form does not exceed about 25 wt %). In yet another embodiment, the HMG-CoA reductase inhibitor in the solid amorphous dispersion is "almost completely amorphous," meaning that the amount of HMG-CoA reductase inhibitor in amorphous form is at least about 90 wt % (that is, the amount in crystalline form does not exceed about 10 wt %). Amounts of crystalline HMG-CoA reductase inhibitor may be measured by PXRD, SEM analysis, DSC, or any other standard quantitative measurement.

The amorphous HMG-CoA reductase inhibitor can exist within the solid amorphous dispersion in relatively pure amorphous drug domains or regions, as a solid solution of drug homogeneously distributed throughout the polymer or any combination of these states or those states that lie intermediate between them.

Preferably, the amorphous HMG-CoA reductase inhibitor in the solid amorphous dispersion is substantially homogeneous. Preferably, the fraction of HMG-CoA reductase inhibitor that is present in relatively pure amorphous drug domains or regions within the solid amorphous dispersion is on the order of less than about 20 wt %, and preferably less than about 10 wt % of the total amount of HMG-CoA reductase inhibitor.

In another embodiment, at least a portion of the HMG-CoA reductase inhibitor in the solid amorphous dispersion is crystalline. In yet another embodiment, essentially all of the HMG-CoA reductase inhibitor in the solid amorphous dispersion is crystalline.

When at least portion of the HMG-CoA reductase inhibitor in the solid amorphous dispersion is crystalline, the HMG-CoA reductase inhibitor crystals are preferably small, having an average diameter of about 50 μm or less. The crystals may be smaller than about 10 μm, smaller than about 5 μm, smaller than about 2 μm, smaller than about 1 μm, or even smaller than about 0.1 μm in average diameter.

In one embodiment the solid amorphous dispersion of the present invention comprises (1) a CETP inhibitor, (2) an acid sensitive HMG-CoA reductase inhibitor, and (3) a concentration-enhancing polymer, wherein at least about 60 wt % of the CETP inhibitor is in an amorphous form and wherein the HMG-CoA reductase inhibitor is either amorphous or crystalline. In another embodiment, the solid amorphous dispersion of the present invention comprises (1) a CETP inhibitor, (2) an acid sensitive HMG-CoA reductase inhibitor, and (3) a concentration-enhancing polymer, wherein at least about 60 wt % of the CETP inhibitor is in an amorphous form and wherein at least about 60 wt % of the HMG-CoA reductase inhibitor is in an amorphous form. In yet another embodiment, the solid amorphous dispersion of the present invention comprises (1) a CETP inhibitor, (2) an acid sensitive HMG-CoA reductase inhibitor, and (3) a concentration-enhancing polymer, wherein at least about 90 wt % of the CETP inhibitor is in an amorphous form and wherein the HMG-CoA reductase inhibitor is either amorphous or crystalline. In yet another embodiment, the solid amorphous dispersion of the present invention comprises (1) a CETP inhibitor, (2) an acid sensitive HMG-CoA reductase inhibitor, and (3) a concentration-enhancing polymer, wherein at least about 90 wt % of the CETP inhibitor is in an amorphous form and wherein at least about 90 wt % of the HMG-CoA reductase inhibitor is in an amorphous form. In yet another embodiment, the solid amorphous dispersion of the present invention comprises (1) a CETP inhibitor, (2) an acid sensitive HMG-CoA reductase inhibitor, and (3) a concentration-enhancing polymer, wherein at least about 90 wt % of the CETP inhibitor is in an amorphous form, at least about 90 wt % of the HMG-CoA reductase inhibitor is in an amorphous form, and wherein the CETP inhibitor is homogeneously dispersed throughout the polymer. In yet another embodiment, the solid amorphous dispersion of the present invention comprises (1) a CETP inhibitor, (2) an acid sensitive HMG-CoA reductase inhibitor, and (3) a concentration-enhancing polymer, wherein at least about 90 wt % of the CETP inhibitor is in an amorphous form, at least about 90 wt % of the HMG-CoA reductase inhibitor is in an amorphous form, and wherein both the CETP inhibitor and the HMG-CoA reductase inhibitor are homogeneously dispersed throughout the polymer.

The relative amounts of CETP inhibitor and HMG-CoA reductase inhibitor present in the solid amorphous dispersion will vary depending on the desired dose for each compound, which in turn, depends on the potency of the compound and the condition being treated. For example, the desired daily dose for the CETP inhibitor torcetrapib ranges from 1 mg/day to 1000 mg/day, preferably 10 to 250 mg/day, more preferably 30 to 90 mg/day. For the HMG-CoA reductase inhibitor atorvastatin calcium, the dose ranges from 1 to 160 mg/day, preferably 2 to 80 mg/day. For the HMG-CoA reductase inhibitors lovastatin, pravastatin sodium, simvastatin, rosuvastatin calcium, and fluvastatin sodium, the dose ranges from 2 to 160 mg/day, preferably 10 to 80 mg/day. For high-potency HMG-CoA reductase inhibitors, the dose can range from 0.05 to 2 mg/day.

In a specific preferred embodiment, the CETP inhibitor is torcetrapib and the HMG-CoA reductase inhibitor is atorvastatin calcium or pharmaceutically acceptable forms thereof. For these compounds, it is preferred that the weight ratio of CETP inhibitor to HMG-CoA reductase inhibitor in the solid amorphous dispersion range from about 0.1 to about 36, preferably about 0.3 to about 20, more preferably about 0.5 to about 18.

The combined amount of CETP inhibitor and HMG-CoA reductase inhibitor in the solid amorphous dispersion may range from about 1 to about 90 wt % of the total mass of the dispersion, depending on the desired doses of the two compounds and the effectiveness of the concentration-enhancing polymer. To limit the size of a dosage form made from the solid amorphous dispersion to achieve a given dose, it is generally preferred that the combined amount of CETP inhibitor and HMG-CoA reductase inhibitor be about 5 wt % or more, and more preferably about 10 wt % or more of the total mass of the dispersion. Higher combined amounts of CETP inhibitor and HMG-CoA reductase inhibitor may also be used, such as about 25 wt % or more, about 40 wt % or more, and even about 50 wt % or more of the total mass of the dispersion.

However, there must be sufficient concentration-enhancing polymer present in the solid amorphous dispersion to obtain concentration enhancement of the CETP inhibitor when the dispersion is administered to an aqueous use environment. Thus, the combined amount of CETP inhibitor and HMG-CoA reductase inhibitor may be about 80 wt % or less, or even about 60 wt % or less. The solid amorphous dispersion may contain higher combined amounts of CETP inhibitor and HMG-CoA reductase inhibitor, provided there is sufficient concentration-enhancing polymer present to result in concentration enhancement of the CETP inhibitor.

Concentration-Enhancing Polymers

The concentration-enhancing polymer is selected from the group consisting of neutral polymers, neutralized acidic polymers, and mixtures thereof. Polymers suitable for use in the solid amorphous dispersions of the present invention should be inert, in the sense that they do not chemically react with the CETP inhibitor or HMG-CoA reductase inhibitor in an adverse manner, are pharmaceutically acceptable, and should have an aqueous-solubility of at least about 0.1 mg/mL over at least a portion of the pH range of 1-8.

In one embodiment, the concentration-enhancing polymer is "neutral," meaning that the concentration-enhancing polymer possesses substantially no acidic functional groups. By "substantially no acidic functional groups" is meant that the number of acidic groups covalently attached to the polymer is less than about 0.05 milliequivalents per gram of polymer. Preferably, the number is less than about 0.02 milliequivalents per gram of polymer. By "acidic groups" is meant functional groups that, when attached to the polymer, have pKa values in a humid or aqueous environment of about 5 or less. Preferably, the pKa value of the functional groups on the neutral polymer is greater than about 6. Thus, the neutral polymers may contain ionic groups as long as the groups are not acidic.

In another embodiment, the neutral polymer is substantially nonionizable. By "substantially nonionizable" is meant that the number of "ionizable groups" covalently attached to the polymer is less than about 0.05 milliequivalents per gram of polymer and preferably less than about 0.02 milliequivalents per gram of polymer. "Ionizable groups" are those that are at least about 10% ionized over at least a portion of the physiologically relevant pH 1 to 8 range and thus such groups have pKa values of about 0 to 9.

The polymer may be cellulosic or non-cellulosic. By "cellulosic" is meant a cellulose polymer that has been modified by reaction of at least a portion of the hydroxyl groups on the saccharide repeating units with a compound to form an ester or an ether substituent. Generally, the degree of substitution of each substituent group can range from 0.02 to 2.9 as long as the other criteria of the polymer are met. "Degree of substitution" refers to the average number of the three hydroxyls per saccharide repeat unit on the cellulose chain that have been substituted. For example, if all of the hydroxyls on the cellulose chain have been acetate substituted, the acetate degree of substitution is 3.

A polymer name such as "cellulose acetate" (CA) refers to any of the family of cellulosic polymers that have acetate groups attached via ester linkages to a significant fraction of the cellulosic polymer's hydroxyl groups. Also included within each polymer family type are cellulosic polymers that have additional substituents added in relatively small amounts that do not substantially alter the performance of the polymer.

One class of polymers suitable for use with the present invention comprises neutral cellulosic polymers. Exemplary ether-linked substituents suitable for neutral cellulosic polymers include: alkyl groups, such as methyl, ethyl, propyl, butyl, etc.; hydroxy alkyl groups such as hydroxymethyl, hydroxyethyl, hydroxypropyl, etc.; and aryl groups such as phenyl. Exemplary ester-linked substituents include: alkyl groups, such as acetate, propionate, butyrate, etc.; and aryl groups such as phenylate. However, when aryl groups are included, the polymer may need to include a sufficient amount of a hydrophilic substituent so that the polymer has at least some water solubility at any physiologically relevant pH of from 1 to 8.

Exemplary neutral cellulosic polymers include: hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose. Neutral polymers suitable for use in the solid amorphous dispersions of the present invention are more fully disclosed in U.S. Patent Application Publication Number 2003-0091643A1, herein incorporated by reference.

Another class of polymers suitable for use with the present invention comprises neutral non-cellulosic polymers. Exemplary polymers include: vinyl polymers and copolymers having substituents of hydroxyl, alkyacyloxy, or cyclicamido; polyvinyl alcohols that have at least a portion of their repeat units in the unhydrolyzed (vinyl acetate) form; polyvinyl alcohol polyvinyl acetate copolymers; polyvinyl pyrrolidone (also known as povidone or PVP); polymethacrylates copolymers, such as copolymers of ethyl acrylate and methylmethacrylate; polyoxyethylene-polyoxypropylene copolymers, also known as poloxamers; and polyethylene polyvinyl alcohol copolymers.

In another embodiment, the concentration-enhancing polymer is a neutralized acidic polymer. By "neutralized acidic polymer" is meant any acidic polymer for which a significant fraction of the "acidic moieties" or "acidic substituents" have been "neutralized"; that is, exist in their deprotonated form. By "acidic polymer" is meant any polymer that possesses a significant number of acidic moieties. In general, a significant number of acidic moieties would be greater than or equal to about 0.05 milliequivalents of acidic moieties per gram of polymer. "Acidic moieties" include any functional groups that are sufficiently acidic that, in contact with or dissolved in water, can at least partially donate a hydrogen cation to water and thus increase the hydrogen-ion concentration. This definition includes any functional group or "substituent," as it is termed when the functional group is covalently attached to a polymer that has a pKa of less than about 10. Exemplary classes of functional groups that are included in the above description include carboxylic acids, thiocarboxylic acids, phosphates, phenolic groups, and sulfonates. Such functional groups may make up the primary structure of the polymer such as for polyacrylic acid, but more generally are covalently attached to the backbone of the parent polymer and thus are termed "substituents." Neutralized acidic polymers are described in more detail U.S. Patent Application Publication Number 2003-0054038A1, the relevant disclosure of which is incorporated by reference.

The "degree of neutralization," $\alpha$, of a polymer substituted with monoprotic acids (such as carboxylic acids) is defined as the fraction of the acidic moieties on the polymer that have been neutralized; that is, deprotonated by a base. The degree to which the acidic moieties on the polymer are neutralized by the base is dependent on (1) the ratio of the number of milliequivalents of base per gram of polymer divided by the number of milliequivalents of acidic moieties per gram of polymer and (2) the relative $pK_a$s of the base and the acidic polymer. When the $pK_a$ of the base is much higher than the $pK_a$ of the acidic moieties of the acidic polymer (that is, the ratio of the $pK_a$ of the base to the $pK_a$ of the polymer), then each milliequivalent of base will approximately neutralize one milliequivalent of acid. Thus, if 0.5 milliequivalent of a strong base per gram of polymer is added to an acidic polymer with 1.0 milliequivalents of acidic moieties per gram of polymer, then the degree of neutralization is roughly equal to 0.5.

If a relatively weak base with a $pK_a$ value roughly equal to that of the polymer's acidic moieties is used to neutralize the polymer (e.g., the base is the sodium salt of an aliphatic carboxylic acid, such as sodium propionate, and the acidic groups on the polymer are aliphatic carboxylic acids, such as succinate), then more base must be added to achieve the same extent of neutralization. Thus, if 1.0 milliequivalent of a base per gram of polymer, with a $pK_a$ roughly equal to the $pK_a$ of the polymer, is added to an acidic polymer with 1.0 milliequivalents of acidic moieties per gram of polymer, then the degree of neutralization is roughly also equal to 0.5.

When the degree of neutralization, α, is less than 0.9, it may be approximated by the following equation:

$$\alpha = \frac{E_{base}}{E_{polymer}} \cdot \frac{10^{pKa,Base-pKa,Polymer}}{1+10^{pKa,Base-pKa,Polymer}}$$

where $E_{base}$ is the number of milliequivalents of base per gram of polymer, $E_{polymer}$ is the number of milliequivalents of acidic moieties (of the polymer) per gram of polymer, and $pK_a$,Base and $pK_a$,Polymer are the $pK_a$ values of the base and polymer, respectively. It should be noted that if the calculated value of a from this equation is greater than 1, the degree of neutralization can be considered essentially 1, meaning that essentially all of the acidic moieties on the polymer have been neutralized.

Alternatively, the degree of neutralization may be measured experimentally. Although not strictly applicable to organic solutions or solid dispersions, the Henderson-Hasselbach equation can be used to relate the effective pH of an aqueous solution or a hydrated suspension to the degree of neutralization. According to this equation the effective pH of the solution or hydrated suspension is given as:

pH=$pK_a$,Polymer−log [(1−α)/α]

Typically, for an acidic polymer to be considered a "neutralized acidic polymer," α must be at least about 0.001 (or 0.1%), preferably about 0.01 (1%) and more preferably at least about 0.1 (10%). Such small degrees of neutralization may be acceptable because often the effective pH of the polymer changes dramatically with small increases in the degree of neutralization. Nonetheless, even greater degrees of neutralization are even more preferred. Thus, α is preferably at least about 0.5 (meaning that at least about 50% of the acidic moieties have been neutralized) and α is more preferably at least about 0.9 (meaning that at least about 90% of the acidic moieties have been neutralized).

Often the most chemically stable compositions are formed when approximately 100% of the acidic groups of the polymer have been neutralized, that is, α is approximately equal to 1.0. In some cases stable dispersions are formed when excess base is present.

Neutralized acidic polymers may be either cellulosic or non-cellulosic as described above. A preferred class of acidic polymers consists of cellulosic polymers with at least one ester- and/or ether-linked acidic substituent in which the polymer has a degree of substitution of at least about 0.02 for the acidic substituent. Generally, the degree of substitution of each substituent group can range from about 0.02 to 2.9 as long as the other criteria of the polymer are met. More typically, the degree of substitution for each substituent is from about 0.1 to 2.0.

Exemplary acidic, ether-linked ionizable substituents include: carboxylic acids, such as carboxymethoxy (commonly referred to as carboxymethyl), carboxyethoxy (commonly referred to as carboxyethyl), carboxypropoxy (commonly referred to as carboxypropyl), and carboxyphenoxy (commonly referred to as carboxyphenyl), salicylic acid (attached to the cellulosic polymer via the phenolic hydroxyl), alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid such as ethoxynicotinic acid, and the various isomers of picolinic acid such as ethoxypicolinic acid, etc.; thiocarboxylic acids, such as thioacetic acid; substituted phenoxy groups, such as hydroxyphenoxy, etc.; phosphates, such as ethoxy phosphate; and sulfonates, such as ethoxy sulphonate.

Exemplary ester-linked ionizable substituents include: carboxylic acids, such as succinate, citrate, phthalate, terephthalate, isophthalate, trimellitate, and the various isomers of pyridinedicarboxylic acid, etc.; thiocarboxylic acids, such as thiosuccinate; substituted phenoxy groups, such as amino salicylic acid; phosphates, such as acetyl phosphate; and sulfonates, such as acetyl sulfonate. For aromatic-substituted polymers to also have the requisite aqueous solubility, it is also desirable that sufficient hydrophilic groups such as hydroxypropyl or carboxylic acid functional groups be attached to the polymer to render the polymer aqueous soluble at least at pH values where any ionizable groups are ionized. In some cases, the aromatic group may itself be ionizable, such as phthalate or trimellitate substituents.

Exemplary acidic cellulosic polymers include such polymers as carboxyethyl cellulose, carboxymethyl cellulose, carboxymethyl ethyl cellulose, cellulose succinate, cellulose acetate succinate, hydroxyethyl cellulose succinate, hydroxyethyl cellulose acetate succinate, hydroxyethyl methyl cellulose succinate, hydroxyethyl methyl cellulose acetate succinate, hydroxypropyl cellulose succinate, hydroxypropyl cellulose acetate succinate, hydroxypropyl methyl cellulose acetate succinate, hydroxypropyl methyl cellulose succinate, cellulose phthalate, cellulose acetate phthalate, methyl cellulose acetate phthalate, ethyl cellulose acetate phthalate, cellulose propionate phthalate, hydroxyethyl methyl cellulose acetate phthalate, hydroxypropyl cellulose acetate phthalate, hydroxypropyl methyl cellulose phthalate, hydroxypropyl methyl cellulose acetate phthalate, hydroxypropyl cellulose acetate phthalate succinate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Alternatively, the acidic polymer may be non-cellulosic. Exemplary acidic non-cellulosic polymers include carboxylic acid-functionalized vinyl polymers, such as the carboxylic acid functionalized polymethacrylates and carboxylic acid functionalized polyacrylates such as the EUDRAGITS® manufactured by Rohm Tech, Inc., of Malden, Mass.; and carboxylic acid functionalized starches such as starch glycolate.

Neutralized acidic polymers may be formed by any conventional method known in the art that results in the desired degree of neutralization. In general, the acidic polymer is neutralized through the addition of a sufficient amount of base to a solution or composition containing the acidic polymer. The polymer may be neutralized prior to formation of the solid amorphous dispersion. For example, a base may be added to a solution of the acidic polymer resulting in neutralization of the polymer's acidic functional groups. Alternatively, the acidic polymer may be neutralized during formation of the solid amorphous dispersion, or may be neutralized following formation of the solid amorphous dispersion.

A wide range of bases may be used to neutralize the acidic polymer. The term "base" is used broadly to include not only strong bases such as sodium hydroxide, but also weak bases and buffers that are capable of achieving the desired degree of neutralization. Examples of bases include hydroxides, such as sodium hydroxide, potassium hydroxide, calcium hydroxide, ammonium hydroxide, and choline hydroxide; bicarbonates, such as sodium bicarbonate, potassium bicarbonate, and ammonium bicarbonate; carbonates, such as ammonium carbonate, calcium carbonate, and sodium carbonate; amines, such as tris(hydroxymethyl)amino methane, ethanolamine, diethanolamine, N-methyl glucamine, glucosamine, ethylenediamine, N,N'-dibenzylethylenediamine, N-benzyl-2-phenethylamine, cyclohexylamine, cyclopentylamine, diethylamine, isopropylamine, diisopropylamine, dodecylamine, and triethylamine; proteins, such as gelatin; basic forms of amino acids such as lysine, arginine, guanine, glycine, and adenine; polymeric amines, such as polyamino methacrylates, such as Eudragit E; conjugate bases of various acids, such as sodium acetate, sodium benzoate, ammonium acetate, disodium phosphate, trisodium phosphate, calcium acetate, calcium hydrogen phosphate, sodium phenolate, sodium sulfate, ammonium chloride, and ammonium sulfate; salts of EDTA, such as tetra sodium EDTA; and salts of various acidic polymers such as sodium starch glycolate, sodium carboxymethyl cellulose and sodium polyacrylic acid. The use of the bicarbonates is in some cases preferred, as these generate carbon dioxide during the neutralization process, which can be removed easily following neutralization.

While specific polymers have been discussed as being suitable for use in the compositions of the present invention, blends of such polymers may also be suitable. Thus the term "polymer" is intended to include blends of polymers in addition to a single species of polymer.

Of all of the foregoing polymers, those most especially preferred include the neutral polymers polyvinyl pyrrolidone, poloxamers, hydroxypropyl methyl cellulose acetate, hydroxypropyl methyl cellulose, hydroxypropyl cellulose, and hydroxyethyl cellulose acetate; neutralized forms of the following acidic polymers: hydroxypropyl methyl cellulose acetate succinate, hydroxypropyl methyl cellulose phthalate, cellulose acetate phthalate, cellulose acetate trimellitate, and carboxymethyl ethyl cellulose; and blends thereof.

Preparation of Dispersions

The solid amorphous dispersions comprising a CETP inhibitor, an HMG-CoA reductase inhibitor, and a concentration-enhancing polymer may be made according to any conventional process for forming solid amorphous dispersions that results in at least a major portion (at least about 60 wt %) of the CETP inhibitor being in the amorphous state. Such processes include mechanical, thermal and solvent processes. Exemplary mechanical processes include milling and extrusion; melt processes including high temperature fusion, solvent-modified fusion and melt-congeal processes; and solvent processes including non-solvent precipitation, spray-coating and spray-drying. See, for example, the following U.S. Patents, the pertinent disclosures of which are incorporated herein by reference: U.S. Pat. Nos. 5,456,923 and 5,939,099, which describe forming dispersions by extrusion processes; U.S. Pat. Nos. 5,340,591 and 4,673,564, which describe forming dispersions by milling processes; and U.S. Pat. Nos. 5,707,646 and 4,894,235, which describe forming dispersions by melt congeal processes.

One preferred method for forming the solid amorphous dispersions of the present invention is by "solvent processing," which consists of dissolution of the CETP inhibitor, one or more concentration-enhancing polymers, and optionally the HMG-CoA reductase inhibitor in a common solvent. "Common" here means that the solvent, which can be a mixture of compounds, will dissolve the CETP inhibitor and the polymer(s). The HMG-CoA reductase inhibitor may be dissolved, partially dissolved, or suspended in the common solvent. Once the solution comprising the CETP inhibitor, the HMG-CoA reductase inhibitor, the polymer and the solvent has been formed, the solvent is rapidly removed by evaporation or by mixing with a non-solvent. Exemplary processes are spray-drying, spray-coating (pan-coating, fluidized bed coating, etc.), and precipitation by rapid mixing of the polymer and drug solution with $CO_2$, water, or some other non-solvent. Preferably, removal of the solvent results in the formation of a substantially homogeneous, solid amorphous dispersion.

Solvents suitable for solvent processing can be any compound in which the CETP inhibitor, the concentration-enhancing polymer, and optionally, the HMG-CoA reductase inhibitor are mutually soluble. Preferably, the solvent is also volatile with a boiling point of 150° C. or less. In addition, the solvent should have relatively low toxicity and be removed from the solid amorphous dispersion to a level that is acceptable according to The International Committee on Harmonization (ICH) guidelines. Removal of solvent to this level may require a subsequent processing step such as tray-drying. Preferred solvents include water; alcohols such as methanol, ethanol, 1-propanol, 2-propanol, the various isomers of butanol, 1-pentanol, and 2-methyl-1-propanol; ketones such as acetone, methyl ethyl ketone, methyl iso-butyl ketone, cyclohexanone; esters, such as methyl acetate, ethyl formate, ethyl acetate, propyl acetate, and butyl acetate; ethers, such as dimethyl ether, ethyl ether, tert-butyl-methyl ether, 1,2, dimethoxyethane, 2-ethoxyethanol, 2-methoxyethanol, tetrahydrofuran, methyl tetrahydrofuran, 1,3-dioxolane, and 1,4-dioxane; alkanes, such as butane, pentane, hexane, heptane, cyclohexane, and methylcyclohexane; alkenes, such as pentene, hexene, and cyclohexene; nitriles, such as acetonitrile; alkyl halides, such as methylene chloride, chloroform, dichloroethane, dichloroethene, trichloroethane, and trichloroethylene; aromatics, such as benzene, toluene, xylene, ethylbenzene, anisole, cumene, and chlorobenzene; pyridine; and mixtures thereof. Lower volatility solvents such as dimethyl acetamide or dimethylsulfoxide can also be used in small amounts in mixtures with a volatile solvent. Mixtures of solvents, such as 50% methanol and 50% acetone, can also be used, as can mixtures with water. Preferred solvents include acetone, methyl ethyl ketone, methyl isobutyl ketone, methanol, ethanol, 1-propanol, 2-propanol, methyl acetate, ethyl acetate, toluene, methylene chloride, tetrahydrofuran, 1,4-dioxane, 1,3-dioxolane, and mixtures thereof. Most preferred solvents include acetone, methanol, ethanol, 1-propanol, 2-propanol, ethyl acetate, and mixtures thereof. Mixtures of the above with water may also be used.

The solvent may be removed by spray-drying. The term "spray-drying" is used conventionally and broadly refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's Chemical Engineers' Handbook, pages 20-54 to 20-57 (Sixth Edition 1984). More details on spray-drying processes and equipment are reviewed by Marshall, "Atomization and Spray-Drying," 50 Chem. Eng. Prog. Monogr. Series 2 (1954), and Masters, Spray Drying Handbook (Fourth Edition 1985). The strong driving force for solvent evaporation is generally provided by maintaining the partial pressure of solvent in the spray-drying apparatus well below the vapor pressure of the solvent at the temperature of the drying droplets. This is accomplished by (1) maintaining the pressure in the spray-drying apparatus at a partial vacuum (e.g., 0.01 to 0.50 atm); or (2) mixing the liquid droplets with a warm drying gas; or (3) both (1) and (2). In addition, at least a portion of the heat required for evaporation of solvent may be provided by heating the spray solution.

The solvent-bearing feed, comprising the CETP inhibitor, the HMG-CoA reductase inhibitor, and the concentration-enhancing polymer, can be spray-dried under a wide variety of conditions and yet still yield dispersions with acceptable properties. For example, various types of nozzles can be used to atomize the spray solution, thereby introducing the spray solution into the spray-dry chamber as a collection of small droplets. Essentially any type of nozzle may be used to spray the solution as long as the droplets that are formed are sufficiently small that they dry sufficiently (due to evaporation of solvent) that they do not stick to or coat the spray-drying chamber wall.

Although the maximum droplet size varies widely as a function of the size, shape and flow pattern within the spray-dryer, generally droplets should be less than about 500 μm in diameter when they exit the nozzle. Examples of types of nozzles that may be used to form the solid amorphous dispersions include the two-fluid nozzle, the fountain-type nozzle, the flat fan-type nozzle, the pressure nozzle and the rotary atomizer. In a preferred embodiment, a pressure nozzle is used, as disclosed in detail in commonly assigned copending U.S. application Ser. No. 10/351,568, the disclosure of which is incorporated herein by reference.

The spray solution can be delivered to the spray nozzle or nozzles at a wide range of temperatures and flow rates. Generally, the spray solution temperature can range anywhere from just above the solvent's freezing point to about 20° C. above its ambient pressure boiling point (by pressurizing the solution) and in some cases even higher. Spray solution flow rates to the spray nozzle can vary over a wide range depending on the type of nozzle, spray-dryer size and spray-dry conditions such as the inlet temperature and flow rate of the drying gas. Generally, the energy for evaporation of solvent from the spray solution in a spray-drying process comes primarily from the drying gas.

The drying gas can, in principle, be essentially any gas, but for safety reasons and to minimize undesirable oxidation of the drug or other materials in the solid amorphous dispersion, an inert gas such as nitrogen, nitrogen-enriched air or argon is utilized. The drying gas is typically introduced into the drying chamber at a temperature between about 60° and about 300° C. and preferably between about 80° and about 240° C.

The large surface-to-volume ratio of the droplets and the large driving force for evaporation of solvent leads to rapid solidification times for the droplets. Solidification times should be less than about 20 seconds, preferably less than about 10 seconds, and more preferably less than about 1 second. This rapid solidification is often critical to the particles maintaining a uniform, homogeneous dispersion instead of separating into CETP inhibitor-rich and polymer-rich phases. In a preferred embodiment, the height and volume of the spray-dryer are adjusted to provide sufficient time for the droplets to dry prior to impinging on an internal surface of the spray-dryer, as described in detail in U.S. Pat. No. 6,763,607, incorporated herein by reference.

Following solidification, the solid powder typically stays in the spray-drying chamber for about 5 to 60 seconds, further evaporating solvent from the solid powder. The final solvent content of the solid dispersion as it exits the dryer should be low, since this reduces the mobility of the CETP inhibitor molecules in the solid amorphous dispersion, thereby improving its stability. Generally, the solvent content of the solid amorphous dispersion as it leaves the spray-drying chamber should be less than about 10 wt % and preferably less than about 2 wt %. Following formation, the solid amorphous dispersion can be dried to remove residual solvent using suitable drying processes, such as tray drying, fluid bed drying, microwave drying, belt drying, rotary drying, vacuum drying, and other drying processes known in the art.

The solid amorphous dispersion is usually in the form of small particles. The volume mean size of the particles may be less than about 500 μm in diameter, or less than about 100 μm in diameter, less than about 50 μm in diameter or less than about 25 μm in diameter. When the solid amorphous dispersion is formed by spray-drying, the resulting dispersion is in the form of such small particles. When the solid amorphous dispersion is formed by other methods such by melt-congeal or extrusion processes, the resulting dispersion may be sieved, ground, or otherwise processed to yield a plurality of small particles.

Once the solid amorphous dispersion comprising the CETP inhibitor, the HMG-CoA reductase inhibitor, and the concentration-enhancing polymer has been formed, several processing operations can be used to facilitate incorporation of the dispersion into a dosage form. These processing operations include drying, granulation, and milling.

The solid amorphous dispersion may be granulated to increase particle size and improve handling of the dispersion while forming a suitable dosage form. Preferably, the average size of the granules will range from 50 to 1000 μm. Such granulation processes may be performed before or after the composition is dried, as described above. Dry or wet granulation processes can be used for this purpose. An example of a dry granulation process is roller compaction. Wet granulation processes can include so-called low shear and high shear granulation, as well as fluid bed granulation. In these processes, a granulation fluid is mixed with the composition after the dry components have been blended to aid in the formation of the granulated composition. Examples of granulation fluids include water, ethanol, isopropyl alcohol, n-propanol, the various isomers of butanol, and mixtures thereof.

If a wet granulation process is used, the granulated composition is often dried prior to further processing. Examples of suitable drying processes to be used in connection with wet granulation are the same as those described above. Where the solid amorphous dispersion is made by a solvent process, the composition can be granulated prior to removal of residual solvent. During the drying process, residual solvent and granulation fluid are concurrently removed from the composition.

Once the composition has been granulated, it may then be milled to achieve the desired particle size. Examples of suitable processes for milling the composition include hammer milling, ball milling, fluid-energy milling, roller milling, cutting milling, and other milling processes known in the art.

Although the key ingredients in the solid amorphous dispersion are the CETP inhibitor, the HMG-CoA reductase inhibitor, and the concentration-enhancing polymer, the inclusion of other excipients in the dispersion may be useful and even preferred. When the solid amorphous dispersion is made by solvent processing, these excipients may be dissolved, partially dissolved, or suspended in the common solvent.

One very useful class of excipients is surfactants, preferably present from 0 to 10 wt % in the solid amorphous dispersion. Suitable surfactants include fatty acid and alkyl sulfonates; commercial surfactants such as benzalkonium chloride (HYAMINE® 1622 from Lonza, Inc. of Fairlawn, N.J.); dioctyl sodium sulfosuccinate (DOCUSATE SODIUM from Mallinckrodt Specialty Chemicals of St. Louis, Mo.); polyoxyethylene sorbitan fatty acid esters (TWEEN® from ICI Americas Inc. of Wilmington, Del.; LIPOSORB® O 20 from Lipochem Inc. of Patterson N.J.; CAPMUL® POE 0 from Abitec Corp. of Janesville, Wis.); natural surfactants such as sodium taurocholic acid, 1 palmitoyl-2-oleoyl-sn-glycero-3-phosphocholine, lecithin, and other phospholipids and mono- and diglycerides; and polyoxyethylene-polyoxypropylene (also known as poloxamers). Such materials can advantageously be employed to increase the rate of dissolution by, for example, facilitating wetting.

Inclusion of pH modifiers such as acids, bases, or buffers may also be beneficial in an amount of from 0 to 10 wt % of the solid amorphous dispersion. In one embodiment, the solid amorphous dispersion includes a base. The inclusion of a base can locally raise the pH in the dispersion, leading to an improvement in chemical stability of the HMG-CoA reductase inhibitor. The term "base" is used broadly to include not only strong bases such as sodium hydroxide, but also weak bases and buffers that are capable of achieving the desired increase chemical stability. Examples of bases include hydroxides, such as sodium hydroxide, calcium hydroxide, ammonium hydroxide, and choline hydroxide; bicarbonates, such as sodium bicarbonate, potassium bicarbonate, and ammonium bicarbonate; carbonates, such as ammonium carbonate, calcium carbonate, and sodium carbonate; amines, such as tris(hydroxymethyl)amino methane, ethanolamine, diethanolamine, N methyl glucamine, glucosamine, ethylenediamine, N,N' dibenzylethylenediamine, N benzyl-2-phenethylamine, cyclohexylamine, cyclopentylamine, diethylamine, isopropylamine, diisopropylamine, dodecylamine, and triethylamine; proteins, such as gelatin; amino acids such as lysine, arginine, guanine, glycine, and adenine; polymeric amines, such as polyamino methacrylates, such as Eudragit E; conjugate bases of various acids, such as sodium acetate, sodium benzoate, ammonium acetate, disodium phosphate, trisodium phosphate, calcium acetate, calcium hydrogen phosphate, sodium phenolate, sodium sulfate, ammonium chloride, and ammonium sulfate; salts of EDTA, such as tetra sodium EDTA; and salts of various acidic polymers such as sodium starch glycolate, sodium carboxymethyl cellulose and sodium polyacrylic acid.

Concentration Enhancement

The polymer used in the solid amorphous dispersion is a "concentration-enhancing polymer," meaning that it meets at least one, and preferably both, of the following conditions.

The first condition is that the concentration-enhancing polymer increases the maximum drug concentration (MDC) of the CETP inhibitor in the environment of use relative to a control composition consisting of an equivalent amount of the CETP inhibitor in undispersed form (with no polymer). That is, once the solid amorphous dispersion comprising the CETP inhibitor, the HMG-CoA reductase inhibitor, and concentration-enhancing polymer is introduced into an environment of use, the polymer increases the aqueous concentration of CETP inhibitor relative to the control composition. It is to be understood that the control composition is free from solubilizers or other components that would materially affect the solubility of the CETP inhibitor, and that the CETP inhibitor is in solid form in the control composition. The control composition is conventionally the undispersed CETP inhibitor alone in its lowest energy form, or a mixture of the undispersed CETP inhibitor in its lowest energy form and undispersed HMG-CoA reductase inhibitor in its lowest energy form, but with no concentration-enhancing polymer. The lowest energy form is either the lowest energy crystalline form, or the amorphous form if the crystalline form is unknown. Preferably, the polymer increases the MDC of the CETP inhibitor in aqueous solution by at least about 1.25-fold relative to a control composition, more preferably by at least about 2-fold, and most preferably by at least about 3-fold. Surprisingly, the polymer may achieve extremely large enhancements in aqueous concentration. In some cases, the MDC of CETP inhibitor provided by the test composition is at least about 10-fold, at least about 50-fold, at least about 200-fold, to more than about 500-fold the equilibrium concentration provided by the control.

The second condition is that the concentration-enhancing polymer increases the area under the concentration in the use environment versus time curve (AUC) of the CETP inhibitor in the environment of use relative to a control composition consisting of the undispersed CETP inhibitor but no polymer. (The calculation of an AUC is a well-known procedure in the pharmaceutical arts and is described, for example, in Welling, "Pharmacokinetics Processes and Mathematics," ACS Monograph 185 (1986) for determining the AUC in drug concentration in the blood from in vivo pharmacokinetic data. Similar procedures can be used for determining the AUC in drug concentration from in vitro concentration versus time data.) More specifically, in the environment of use, the solid amorphous dispersion comprising the CETP inhibitor, the HMG-CoA reductase inhibitor, and the concentration-enhancing polymer provides an AUC for the CETP inhibitor in the use environment for any 90-minute period of from about 0 to about 270 minutes following introduction to the use environment that is at least about 1.25-fold that of the control composition described above. Preferably, the AUC for the CETP inhibitor in the use environment provided by the composition is at least about 2-fold, more preferably at least about 3-fold that of the control composition. For some CETP inhibitors, the solid amorphous dispersions of the present invention may provide an AUC value that is at least about 5-fold, at least about 25-fold, at least about 100-fold, and even more than about 250-fold that of a control composition as described above.

As previously mentioned, a "use environment" can be either the in vivo environment, such as the GI tract of an animal, particularly a human, or the in vitro environment of a test solution, such as phosphate buffered saline (PBS) solution or Model Fasted Duodenal (MFD) solution.

Concentration enhancement may be determined through either in vivo tests or through in vitro dissolution tests or by performing an in vitro membrane permeation test as described herein. A composition of the present invention meets the concentration enhancement criteria in at least one of the above test environments.

Where the use environment is the GI tract of an animal, dissolved drug concentration may be determined by a conventional method known in the art. One method is a deconvolution method. In this method, the serum or plasma drug concentration is plotted along the ordinate (y-axis) against the blood sample time along the abscissa (x-axis). The data may then be analyzed to determine drug release rates in the GI tract using any conventional analysis, such as the Wagner-Nelson or Loo-Riegelman analysis. See also Welling, "Pharmacokinetics: Processes and Mathematics" (ACS Monograph 185, Amer. Chem. Soc., Washington, D.C., 1986). Treatment of the data in this manner yields an apparent in vivo drug release profile. Another method is to intubate the patient and periodically sample the GI tract directly.

The solid amorphous dispersions of CETP inhibitor, HMG-CoA reductase inhibitor and concentration-enhancing polymer provide enhanced concentration of the dissolved CETP inhibitor in in vitro dissolution tests. It has been determined that enhanced drug concentration in in vitro dissolution tests in MFD solution or in PBS solution is a good indicator of in vivo performance and bioavailability. In particular, a solid amorphous dispersion of the present invention can be dissolution-tested by adding it to MFD or PBS solution and agitating to promote dissolution.

An in vitro test to evaluate enhanced CETP inhibitor concentration in aqueous solution can be conducted by (1) adding with agitation a sufficient quantity of control composition, typically the undispersed CETP inhibitor alone in its lowest energy form or a mixture of the undispersed CETP inhibitor in its lowest energy form and undispersed HMG-CoA reductase inhibitor in its lowest energy form but with no concentration-enhancing polymer, to the in vitro test medium, such as an MFD or a PBS solution, to achieve equilibrium concentration of the CETP inhibitor; (2) in a separate vessel, adding with agitation a sufficient quantity of test composition (e.g., the solid amorphous dispersion of CETP inhibitor, HMG-CoA reductase inhibitor, and concentration-enhancing polymer) in the same test medium, such that if all the CETP inhibitor dissolved, the theoretical concentration of CETP inhibitor would exceed the equilibrium concentration of the CETP inhibitor by a factor of at least 2, and preferably by a factor of at least 10; and (3) comparing the measured MDC and/or aqueous AUC of CETP inhibitor provided by the test composition in the test medium with the equilibrium concentration, and/or with the aqueous AUC of the CETP inhibitor of the control composition. In conducting such a dissolution test, the amount of test composition or control composition used is an amount such that if all of the CETP inhibitor dissolved the CETP inhibitor concentration would be at least 2-fold, preferably at least 10-fold, and most preferably at least 100-fold that of the equilibrium concentration. Indeed, for some extremely insoluble CETP inhibitors, in order to identify the MDC achieved it may be necessary to use an amount of test composition such that if all of the CETP inhibitor dissolved, the CETP inhibitor concentration would be 1000-fold or even more, that of the equilibrium concentration of the CETP inhibitor.

The concentration of dissolved CETP inhibitor is typically measured as a function of time by sampling the test medium and plotting CETP inhibitor concentration in the test medium vs. time so that the MDC can be ascertained. The MDC is taken to be the maximum value of dissolved CETP inhibitor measured over the duration of the test. The aqueous AUC of the CETP inhibitor is calculated by integrating the CETP inhibitor concentration versus time curve over any 90-minute time period between the time of introduction of the composition into the aqueous use environment (when time equals zero) and 270 minutes following introduction to the use environment (when time equals 270 minutes). Typically, when the composition reaches its MDC rapidly, in say less than about 30 minutes, the time interval used to calculate AUC is from time equals zero to time equals 90 minutes. However, if the AUC of a composition over any 90-minute time period described above meets the criterion of this invention, then the composition formed is considered to be within the scope of this invention.

To avoid large drug particulates that would give an erroneous determination, the test solution is either filtered or centrifuged. "Dissolved drug" is typically taken as that material that either passes a 0.45 µm syringe filter or, alternatively, the material that remains in the supernatant following centrifugation. Filtration can be conducted using a 13 mm, 0.45 µm polyvinylidine difluoride syringe filter sold by Scientific Resources under the trademark TITAN®. Centrifugation is typically carried out in a polypropylene microcentrifuge tube by centrifuging at 13,000 G for 60 seconds. Other similar filtration or centrifugation methods can be employed and useful results obtained. For example, using other types of microfilters may yield values somewhat higher or lower (±10-40%) than that obtained with the filter specified above but will still allow identification of preferred dispersions. It should be recognized that this definition of "dissolved drug" encompasses not only monomeric solvated drug molecules but also a wide range of species such as polymer/drug assemblies that have submicron dimensions such as drug aggregates, aggregates of mixtures of polymer and drug, micelles, polymeric micelles, colloidal particles or nanocrystals, polymer/drug complexes, and other such drug-containing species that are present in the filtrate or supernatant in the specified dissolution test.

An in vitro membrane permeation test may also be used to evaluate the compositions of the present invention. Further details of this membrane permeation test are presented in commonly assigned U.S. Patent Application Ser. No. 60/557,897, entitled "Method and Device for Evaluation of Pharmaceutical Compositions," filed Mar. 30, 2004, the disclosure of which is incorporated herein by reference.

In general terms, an in vitro membrane permeation test to evaluate enhanced drug concentration can be conducted by providing a drug-permeable membrane between feed and permeate reservoirs, as described in detail in the Examples, then (1) administering a sufficient quantity of test composition (that is, the solid amorphous dispersion of CETP inhibitor, HMG-CoA reductase inhibitor, and concentration-enhancing polymer) to a feed test medium, such that if all of the drug dissolved, the theoretical concentration of drug would exceed the equilibrium concentration of the drug by a factor of at least 2; (2) separately adding an equivalent amount of control composition to an equivalent amount of feed test medium; (3) measuring the flux of drug across the membrane from the feed to the permeate reservoir; and (4) determining whether the measured maximum flux of drug provided by the test composition is at least about 1.25-fold that provided by the control composition. A composition of the invention provides concentration enhancement if, when administered to an aqueous use environment, it provides a maximum flux of drug in the above test that is at least about 1.25-fold the maximum flux provided by the control composition. Preferably, the maximum flux provided by the compositions of the invention are at least about 1.5-fold, more preferably at least about 2-fold, and most preferably at least about 3-fold that provided by the control composition.

In another separate aspect, the solid amorphous dispersions, when dosed orally to a human or other animal in a fasted state, provides improved concentration of dissolved CETP inhibitor in the blood relative to the control composition. The solid amorphous dispersion achieves a higher maximum drug concentration ($C_{max}$) of the CETP inhibitor in the blood (serum or plasma) relative the control composition consisting of a mixture of an equivalent amount of undispersed CETP inhibitor in its lowest energy form and an equivalent amount of undispersed HMG-CoA reductase inhibitor in its lowest energy form but with no concentration-enhancing polymer. It is to be understood that the control composition is free from solubilizers or other components that would materially affect the solubility of the CETP inhibitor. Preferably, the solid amorphous dispersion provides a $C_{max}$ of CETP inhibitor in the blood that is at least about 1.25-fold that provided by the control composition, more preferably by at least about 2-fold, and most preferably by at least about 3-fold.

Alternatively, the solid amorphous dispersions, when dosed orally to a human or other animal, provide an AUC in CETP inhibitor concentration in the blood that is at least about 1.25-fold, preferably at least about 2-fold, preferably at least about 3-fold, preferably at least about 4-fold, preferably at least about 6-fold, preferably at least about 10-fold, and even more preferably at least about 20-fold that observed when a control composition consisting of an equivalent quantity of undispersed CETP inhibitor is dosed. It is noted that such compositions can also be said to have a relative bioavailability of from about 1.25-fold to about 20-fold that of the control composition.

Relative bioavailability of CETP inhibitors in the solid amorphous dispersions can be tested in vivo in animals or humans using conventional methods for making such a determination. An in vivo test, such as a crossover study, may be used to determine whether a composition of CETP inhibitor, HMG-CoA reductase inhibitor, and concentration-enhancing polymer provides an enhanced relative bioavailability for the CETP inhibitor compared with a control composition as described above. In an in vivo crossover study a test composition of a solid amorphous dispersion of a CETP inhibitor, an HMG-CoA reductase inhibitor, and polymer is dosed to half a group of test subjects and, after an appropriate washout period (e.g., one week) the same subjects are dosed with a control composition that consists of an equivalent quantity of undispersed CETP inhibitor and undispersed HMG-CoA reductase inhibitor as the test composition (but with no polymer present). The other half of the group is dosed with the control composition first, followed by the test composition. The relative bioavailability of the CETP inhibitor is measured as the concentration in the blood (serum or plasma) versus time area under the curve (AUC) determined for the test group divided by the AUC of the CETP inhibitor in the blood provided by the control composition. Preferably, this test/control ratio is determined for each subject, and then the ratios are averaged over all subjects in the study. In vivo determinations of AUC can be made by plotting the serum or plasma concentration of drug along the ordinate (y-axis) against time along the abscissa (x-axis). To facilitate dosing, a dosing vehicle may be used to administer the dose. The dosing vehicle is preferably water, but may also contain materials for suspending the test or control composition, provided these materials do not dissolve the composition or change the drug solubility in vivo.

In one embodiment, the solid amorphous dispersion comprising a CETP inhibitor, an HMG-CoA reductase inhibitor, and a concentration enhancing polymer, wherein at least a major portion of the CETP inhibitor is amorphous and wherein at least a major portion of the HMG-CoA reductase inhibitor is amorphous, provides concentration enhancement for both the CETP inhibitor and the HMG-CoA reductase inhibitor. In this embodiment, the solid amorphous dispersion, following administration to an in vivo or in vitro aqueous use environment provides at least one of (a) a MDC of the CETP inhibitor and a MDC of the HMG-CoA reductase inhibitor in the use environment that are each at least about 1.25-fold, preferably at least about 2-fold, and more preferably at least about 3-fold that provided by a control composition; and (b) an AUC of the CETP inhibitor and an AUC of said HMG-CoA reductase inhibitor for any period of at least 90 minutes between the time of introduction into the use environment and about 270 minutes following introduction to the use environment that each are at least about 1.25-fold, preferably at least about 2-fold, and more preferably at least about 3-fold that of that provided by a control composition. In this embodiment, the control composition consists of a mixture of an equivalent amount of undispersed CETP inhibitor in its lowest energy form and an equivalent amount of undispersed HMG-CoA reductase inhibitor in its lowest energy form but with no concentration-enhancing polymer. Alternatively, when the solid amorphous dispersion is administered to an in vivo aqueous use environment, the dispersion provides at least one of (c) an AUC in the blood (plasma or serum) of the CETP inhibitor and an AUC in the blood (plasma or serum) of the HMG-CoA reductase inhibitor, that are each at least about 1.25-fold, preferably at least about 2-fold, and more preferably at least about 3-fold those provided by the control composition; and (d) a MDC in the blood (plasma or serum) of the CETP inhibitor and a MDC in the blood (plasma or serum) of the HMG-CoA reductase inhibitor that are each at least about 1.25-fold, preferably at least about 2-fold, and more preferably at least about 3-fold those provided by the control composition.

Chemical Stability

The solid amorphous dispersions of the present invention comprising a CETP inhibitor, an HMG-CoA reductase inhibitor, and a concentration-enhancing polymer exhibit acceptably low rates of degradation of the HMG-CoA reductase inhibitor. In one embodiment, the solid amorphous dispersions of the present invention provide improved chemical stability of the HMG-CoA reductase inhibitor relative to a control dispersion containing the same amount of CETP inhibitor and HMG-CoA reductase inhibitor, but made using the acidic polymer hydroxypropyl methyl cellulose acetate succinate (HPMCAS).

In general, degradation of the HMG-CoA reductase inhibitor may be measured using any conventional method for measuring the potency or purity of drug in a pharmaceutical composition. For example, the amount of active HMG-CoA reductase inhibitor present in a composition may be measured using high-performance liquid chromatography (HPLC) or other analytical techniques well known in the art. Alternatively, the amount of HMG-CoA reductase inhibitor present may be calculated from the amount of drug present in the composition. The potency of the composition is then measured after manufacture of the dispersion or after storage at controlled temperature and humidity conditions for an appropriate period of time. A decrease in potency indicates that a chemical reaction has occurred, leading to a decrease in the amount of active drug present in the composition, and is an indication of poor chemical stability.

An alternative method used to evaluate chemical stability is to analyze the rate of increase in the amount of drug degradant(s) in the composition, which would indicate reaction of the HMG-CoA reductase inhibitor. An HPLC or other analytical technique may be used to determine the concentration of drug degradant(s) in a composition. The amount of the degradant(s) is measured before and after formation of the dispersion or before and after storage under controlled storage conditions. The amount of increase in the drug degradant(s) may be used to determine the amount of decrease in "percent drug purity," defined as 100 times the total amount of drug present divided by the amount of drug initially present. Thus, percent drug purity may be calculated as follows:

$$\text{percent drug purity} = 100 \times \left(\frac{\text{total drug present}}{\text{drug initially present}}\right)$$

When the drug purity is calculated from the total amount of impurities, percent drug purity may be calculated by assuming that the drug initially present, given in wt %, is equal to 100 wt % minus the wt % of total initial impurities, and that total drug present is equal to 100 wt % minus the wt % of total impurities after formation of the dispersion or storage of the dispersion. This method of calculating percent drug purity is by the formula:

$$\text{percent drug purity} = 100 \times \left[1 - \left(\frac{\text{total impurities}}{\text{drug initially present}}\right)\right]$$

The rate at which drug degradation occurs is generally dependent on the conditions used to form the solid amorphous dispersion and on storage conditions. A "degree of degradation" of drug following manufacture or storage may be determined by subtracting the final percent drug purity (determined either by measuring the decrease in drug present or the increase in drug impurities present) from the initial percent drug purity. For example, a sample of dispersion made using 100 mg HMG-CoA reductase inhibitor and having no measurable impurities would have an initial percent drug purity of 100 wt %. If, after forming the solid amorphous dispersion, the amount of HMG-CoA reductase inhibitor in the dispersion decreases to 95 mg, the final percent drug purity would be 95 wt % and the degree of degradation would be 100 wt % less 95 wt %, or 5 wt %. Alternatively, if 100 mg of HMG-CoA reductase inhibitor were found to initially have 1 mg of impurities present, it would have an initial percent drug purity of 99 wt %. If, after formation of the solid amorphous dispersion, the total impurities present had increased to 6 wt %, the final percent drug purity would be 94 wt % and the degree of degradation would be 99 wt % less 94 wt %, or 5 wt %.

Alternatively, degree of degradation can be determined by subtracting the amount of one or more specific drug degradants initially present from the amount of that specific degradant present after manufacture or storage of the dispersion. Such a measure is useful where there are several drug degradants, of which only one or a few is of concern. For example, if an HMG-CoA reductase inhibitor initially contained a specific degradant at a concentration of 1 wt % and after formation of the solid amorphous dispersion the concentration of that degradant was 6 wt %, the degree of degradation would be 6 wt % less 1 wt %, or 5 wt %.

A relative degree of improvement in chemical stability of the HMG-CoA reductase inhibitor in a test composition may be determined by taking the ratio of the degree of degradation of the HMG-CoA reductase inhibitor in a control composition and the degree of degradation of the HMG-CoA reductase inhibitor in a test composition. The test composition is simply the solid amorphous dispersion of the CETP inhibitor, an acid sensitive HMG-CoA reductase inhibitor, and the concentration-enhancing polymer. The control composition consists of the same amount of the CETP inhibitor, the same amount of an acid-sensitive HMG-CoA reductase inhibitor, and the same amount of a concentration-enhancing polymer, except that the concentration-enhancing polymer is the acidic polymer hydroxypropyl methyl cellulose acetate succinate (HMPCAS). For example, where the degree of degradation of the HMG-CoA reductase inhibitor in a test composition is 1 wt %, and the degree of degradation of the HMG-CoA reductase inhibitor in a control composition is 5 wt %, the relative degree of improvement is 5 wt %/1 wt % equals 5.0. For the solid amorphous dispersions of the present invention where the HMG-CoA reductase inhibitor is acid sensitive and the concentration-enhancing polymer is selected from neutral polymers, neutralized polymers, and mixtures thereof, the relative degree of improvement is at least about 1.1. More preferably, the relative degree of improvement is at least about 1.25, more preferably at least about 2.0, and even more preferably at least about 3.0, more preferably at least about 5.0.

An acid sensitive HMG-CoA reductase inhibitor, when formulated in a solid amorphous of the present invention, should be stable at ambient temperature and humidity conditions (e.g., 20% to 60% relative humidity (RH)) for long periods of time, such as months or years. However, to expedite testing, the storage conditions may employ elevated temperature and/or humidity to simulate longer storage times at ambient conditions. The storage time may vary from a few days to weeks or months, depending on the reactivity of the drug and the storage conditions. Where the HMG-CoA reductase inhibitor is particularly acid-sensitive, then shorter storage time periods may be used. Where the rate of degradation is linear, the relative degree of improvement will be independent of the storage time. However, where the rate of degradation is non-linear under controlled storage conditions, a stability test used to compare the test composition with the control composition is preferably chosen such that the degree of degradation is sufficiently large that it may be accurately measured. Typically, the time period is chosen so as to observe a degree of degradation in the control composition of at least 0.1 wt % to 0.2 wt %. However, the time period is not so long that the ratio of HMG-CoA reductase inhibitor to polymer changes substantially. Typically, the time period is such that the observed degree of degradation for the test composition is less than about 50 wt % and preferably less than about 20 wt %. When the rate of degradation in the control composition is relatively slow, the test is preferably conducted over a long enough period of time under controlled storage conditions to allow a meaningful comparison of the stability of the test composition with the control composition.

A stability test which may be used is storage of the test dispersion and the control dispersion for six months at 40° C. and 75% relative humidity (RH) or for 3 months at 50° C. and 75% RH. A relative degree of improvement may become apparent within a shorter time, such as three to five days, and shorter storage times may be used for some very acid-sensitive HMG-CoA reductase inhibitors. When comparing dispersions under storage conditions that approximate ambient conditions, e.g., 30° C. and 60% RH, the storage period may need to be several months or up to two years.

In addition, it is preferred that the solid amorphous dispersion result in chemical stability such that the HMG-CoA reductase inhibitor has a degree of degradation of less than about 5 wt %, more preferably less than about 2 wt %, even more preferably less than about 0.5 wt %, and most preferably less than about 0.1 wt % when stored at 40° C. and 75% RH for six months, or less than about 5 wt %, more preferably less than about 2 wt %, even more preferably less than about 0.5 wt %, and more preferably less than about 0.1 wt %, when stored at 30° C. and 60% RH for one year. Nevertheless, the compositions of the present invention may have a degree of degradation that is much greater than the preferred values, so long as the solid amorphous dispersion achieves the degree of improvement relative to a control composition as described above.

Excipients and Dosage Forms

The solid amorphous dispersion may be combined with optional excipients in order to formulate the composition into tablets, capsules, suspensions, powders for suspension, creams, transdermal patches, depots, and the like. The drug and polymer composition may be added to other dosage form ingredients in essentially any manner that does not substantially alter the drug's activity.

One very useful class of excipients is surfactants. Such materials can advantageously be employed up to 5 wt % to increase the rate of dissolution by facilitating wetting, thereby increasing the MDC, and also to inhibit crystallization or precipitation of drug by interacting with the dissolved drug by mechanisms such as complexation, formation of inclusion complexes, formation of micelles or adsorbing to the surface of solid drug, crystalline or amorphous. Suitable surfactants include fatty acid and alkyl sulfonates, such as sodium lauryl sulfate; commercial surfactants such as benzalkonium chloride (HYAMINE® 1622, available from Lonza, Inc., Fairlawn, N.J.); dioctyl sodium sulfosuccinate, DOCUSATE SODIUM™ (available from Mallinckrodt Spec. Chem., St. Louis, Mo.); polyoxyethylene sorbitan fatty acid esters (TWEEN®, available from ICI Americas Inc., Wilmington, Del.; LIPOSORB® P-20 available from Lipochem Inc., Patterson N.J.; CAPMUL® POE-0 available from Abitec Corp., Janesville, Wis.); natural surfactants such as sodium taurocholic acid, 1-palmitoyl-2-oleoyi-sn-glycero-3-phosphocholine, lecithin, and other phospholipids and mono- and diglycerides; and poloxamers.

Other conventional formulation excipients may be employed in the compositions of the invention, including those excipients well known in the art as described for example in Remington: The Science and Practice of Pharmacy (20$^{th}$ Ed. 2000). Generally, excipients such as matrix materials, diluents, fillers, disintegrating agents, solubilizers, drug complexing agents, pigments, binders, lubricants, glidants, flavorants, and so forth may be used for customary purposes and in typical amounts without adversely affecting the properties of the compositions.

Examples of matrix materials, fillers, or diluents include lactose, mannitol, xylitol, dextrose, sucrose, sorbitol, compressible sugar, microcrystalline cellulose, powdered cellulose, starch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers, and hydroxypropyl methyl cellulose.

Examples of drug-complexing agents or solubilizers include the polyethylene glycols, caffeine, xanthene, gentisic acid and cyclodextrins.

Examples of disintegrants include sodium starch glycolate, sodium carboxymethyl cellulose, calcium carboxymethyl cellulose, croscarmellose sodium, crospovidone (polyvinylpolypyrrolidone), methylcellulose, microcrystalline cellulose, powdered cellulose, starch, pregelatinized starch, and sodium alginate.

Examples of tablet binders include acacia, alginic acid, carbomer, carboxymethyl cellulose sodium, dextrin, ethylcellulose, gelatin, guar gum, hydrogenated vegetable oil, hydroxyethyl cellulose, hydroxypropyl cellulose, hydroxypropyl methyl cellulose, methyl cellulose, liquid glucose, maltodextrin, polymethacrylates, povidone, pregelatinized starch, sodium alginate, starch, sucrose, tragacanth, and zein.

Examples of lubricants include calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc, and zinc stearate.

Examples of glidants include silicon dioxide, talc and cornstarch.

Compositions of the invention may also be used in a wide variety of dosage forms for administration of drugs. Exemplary dosage forms are powders or granules that may be taken orally either dry or reconstituted by addition of water or other liquids to form a paste, slurry, suspension or solution; tablets; capsules; multiparticulates; and pills. Various additives may be mixed, ground, or granulated with the compositions of this invention to form a material suitable for such dosage forms.

Compositions of the invention may be formulated in forms such that they are delivered as a suspension of particles in a liquid vehicle. Such suspensions may be formulated as a liquid or paste at the time of manufacture, or they may be formulated as a dry powder with a liquid, typically water, added at a later time but prior to oral administration. Such powders that are constituted into a suspension are often termed a sachet or an oral powder for constitution (OPC). Such dosage forms can be formulated and reconstituted by any known procedure. The simplest approach is to formulate the dosage form as a dry powder that is reconstituted by simply adding water and agitating. Alternatively, the dosage form may be formulated as a liquid and a dry powder that are combined and agitated to form the oral suspension. In yet another embodiment, the dosage form can be formulated as two powders that are reconstituted by first adding water to one powder to form a solution to which the second powder is combined with agitation to form the suspension.

Generally, it is preferred that the dispersion of drug be formulated for long-term storage in the dry state as this promotes the chemical and physical stability of the drug.

Compositions of the invention may be delivered by a wide variety of routes, including, but not limited to, oral, nasal, rectal, vaginal, subcutaneous, intravenous and pulmonary. Generally, oral delivery is preferred.

Other features and embodiments of the invention will become apparent from the following examples, which are given for illustration of the invention, rather than for limiting its intended scope.

EXAMPLES

Examples 1 and 2

Solid amorphous dispersions of [2R,4S]4-[(3,5-bis-trifluoromethyl-benzyl)-methoxycarbonyl-amino]-2-ethyl-6- trifluoromethyl-3,4-dihydro-2H-quinoline-1-carboxylic acid ethyl ester, also known as torcetrapib, and atorvastatin hemicalcium trihydrate were formed using a potassium-neutralized form of the acidic cellulosic polymer carboxymethyl ethyl cellulose (K+CMEC). The solid amorphous dispersion of Example 1 contained 21.5 wt % torcetrapib, 3.5 wt % atorvastatin hemicalcium trihydrate, and 75 wt % K+CMEC. The solid amorphous dispersion of Example 2 contained 10.75 wt % torcetrapib, 14.25 wt % atorvastatin hemicalcium trihydrate, and 75 wt % K+CMEC. The dispersions of Examples 1 and 2 were formed as follows. First, 937.5 mg carboxymethyl ethyl cellulose (CMEC, available from Freund, Tokyo, Japan) was dissolved in 35 g of methanol/water (80/20 wt/wt) with 534 µL of 1.0 N KOH to neutralize the polymer. Next, for Example 1, 269 mg torcetrapib and 44 mg of atorvastatin hemicalcium trihydrate were dissolved in the mixture to form the spray solution. For Example 2, 134 mg torcetrapib and 178 mg of atorvastatin hemicalcium trihydrate were dissolved in the mixture to form the spray solution. In separate experiments, the solutions were pumped into a "mini" spray-drying apparatus via a Cole Parmer 74900 series rate-controlling syringe pump at a rate of 1.3 ml/min. The drug/polymer solution was atomized through a Spraying Systems Co. two-fluid nozzle, Model No. SU1A using a heated stream of nitrogen at a flow rate of 1 standard cubic feet per minute (SCFM, 28.3 standard L/min). The spray solution was sprayed into an 11-cm diameter stainless steel chamber. The heated gas entered the chamber at an inlet temperature of 70° C. and exited at ambient outlet temperature. The resulting solid amorphous dispersion was collected on filter paper, dried under vacuum, and stored in a desiccator. For Example 1 the yield was 65.3%, and for Example 2 the yield was 68.7%.

The solid amorphous dispersions were analyzed using powder x-ray diffraction (PXRD) using a Bruker AXS D8 Advance diffractometer to determine the amorphous character of the drugs in the dispersions. Samples (approximately 100 mg) were packed in Lucite sample cups fitted with Si(511) plates as the bottom of the cup to give no background signal. Samples were spun in the φ plane at a rate of 30 rpm to minimize crystal orientation effects. The x-ray source (KCu$_\alpha$, λ=1.54 Å) was operated at a voltage of 45 kV and a current of 40 mA. Data for each sample were collected over a period of 27 minutes in continuous detector scan mode at a scan speed of 1.8 seconds/step and a step size of 0.04°/step. Diffractograms were collected over the 2θ range of 4° to 30°. The resulting diffractograms showed none of the sharp peaks characteristic of crystalline drug, but only an amorphous halo. Thus, both the torcetrapib and atorvastatin in the dispersions of Examples 1 and 2 were almost completely amorphous.

An in vitro dissolution test was performed to determine whether the solid amorphous dispersions of Examples 1 and 2 provided concentration-enhancement of torcetrapib and atorvastatin, relative to mixtures containing the crystalline form of each drug. For this test, a sufficient amount of material was added to a microcentrifuge test tube so that the concentration of torcetrapib would have been 1000 µgA/mL, if all of the drug had dissolved. This amount resulted in an atorvastatin concentration of 150 µgA/mL for the solid amorphous dispersion of Example 1 and 1220 µgA/mL for the solid amorphous dispersion of Example 2. The tubes were placed in a 37° C. temperature-controlled chamber, and 1.8 mL PBS at pH 6.5 and 290 mOsm/kg was added to each respective tube. The samples were quickly mixed using a vortex mixer for about 60 seconds. The samples were centrifuged at 13,000 G at 37° C. for 1 minute. The resulting supernatant solution was then sampled and diluted 1:6 (by volume) with methanol and then analyzed by high-performance liquid chromatography (HPLC). The contents of each tube were mixed on the vortex mixer and allowed to stand undisturbed at 37° C. until the next sample was taken. Samples were collected at the times indicated. The results are summarized in Table 1.

Controls 1 and 2

Controls 1 and 2 consisted of physical mixtures of crystalline torcetrapib and crystalline atorvastatin hemicalcium trihydrate. For Control 1, 21.5 mg torcetrapib and 3.5 mg atorvastatin hemicalcium trihydrate were weighed into a scintillation vial and stirred with a spatula, to obtain the same drug ratio as the solid amorphous dispersion of Example 1. For Control 2, 43 mg torcetrapib and 61.8 mg atorvastatin hemicalcium trihydrate were weighed into a scintillation vial and stirred with a spatula, to obtain approximately the same drug ratio as the solid amorphous dispersion of Example 2. The mixtures were blended 15 minutes with a Turbula blender. A sufficient amount of material was added so that the concentration of torcetrapib would have been 1000 µgA/mL, if all of the drug had dissolved. The total atorvastatin concentration would have been 150 µgA/mL for Control 1, and 1320 µgA/mL for Control 2.

The concentrations of drug obtained in these samples were used to determine the maximum concentration of drug ("MDC$_{90}$") and the area under the concentration-versus-time curve ("AUC$_{90}$") during the initial ninety minutes. The results are shown in Table 1.

TABLE 1

| Sample | Torcetrapib Theoretical MDC (µgA/mL) | Torcetrapib MDC$_{90}$ (µgA/mL) | Torcetrapib AUC$_{90}$ (min * µgA/mL) | Atorvastatin Theoretical MDC (µgA/mL) | Atorvastatin MDC$_{90}$ (µgA/mL) | Atorvastatin AUC$_{90}$ (min * µgA/mL) |
|---|---|---|---|---|---|---|
| Example 1 (21.5/3.5/75 torcetrapib/ atorvastatin/ K+CMEC) | 1000 | 376 | 30,100 | 150 | 137 | 11,500 |
| Control 1 (torcetrapib/ atorvastatin physical mixture) | 1000 | <1 | <100 | 150 | 14 | 1,100 |

TABLE 1-continued

| Sample | Torcetrapib Theoretical MDC (μgA/mL) | Torcetrapib MDC$_{90}$ (μgA/mL) | Torcetrapib AUC$_{90}$ (min * μgA/mL) | Atorvastatin Theoretical MDC (μgA/mL) | Atorvastatin MDC$_{90}$ (μgA/mL) | Atorvastatin AUC$_{90}$ (min * μgA/mL) |
|---|---|---|---|---|---|---|
| Example 2 (10.75/14.25/75 torcetrapib/ atorvastatin/ K$^+$CMEC) | 1000 | 600 | 47,700 | 1220 | 766 | 64,800 |
| Control 2 (torcetrapib/ atorvastatin physical mixture) | 1000 | <1 | <100 | 1320 | 263 | 22,700 |

The results show that the solid amorphous dispersions of Examples 1 and 2 provide concentration-enhancement of torcetrapib and atorvastatin, relative to physical mixtures of the same ratios of crystalline drugs. The solid amorphous dispersion of Example 1 provided a MDC$_{90}$ for torcetrapib that was greater than 376-fold that provided by crystalline drug of Control 1, and an AUC$_{90}$ for torcetrapib that was greater than 301-fold that provided by crystalline drug of Control 1. The solid amorphous dispersion of Example 1 also provided a MDC$_{90}$ for atorvastatin that was 9.8-fold that provided by crystalline drug of Control 1, and an AUC$_{90}$ value for atorvastatin that was 10.4-fold that provided by crystalline drug of Control 1. The solid amorphous dispersion of Example 2 provided a MDC$_{90}$ for torcetrapib that was greater than 600-fold that provided by crystalline drug of Control 2, and an AUC$_{90}$ for torcetrapib that was greater than 477-fold that provided by crystalline drug of Control 2. The solid amorphous dispersion of Example 2 also provided a MDC$_{90}$ for atorvastatin that was 2.9-fold that provided by crystalline drug of Control 2, and an AUC$_{90}$ for atorvastatin that was 2.8-fold that provided by crystalline drug of Control 2.

Example 3

A solid amorphous dispersion of torcetrapib and atorvastatin hemicalcium trihydrate was formed using a potassium-neutralized form of the acidic cellulosic polymer hydroxypropyl methyl cellulose acetate succinate (K$^+$HPMCAS-MG). The solid amorphous dispersion of Example 3 contained 7.5 wt % torcetrapib, 2.71 wt % atorvastatin hemicalcium trihydrate, and 89.79 wt % K$^+$HPMCAS-MG. The solid amorphous dispersion of Example 3 was formed as follows. First, 897.1 mg hydroxypropyl methyl cellulose acetate succinate (AQOAT-MG, available from Shin Etsu, Tokyo, Japan) was dissolved in 100 g of acetone with 980 μL of 1.0 N KOH to neutralize the polymer. Next, 75 mg torcetrapib and 27.1 mg of atorvastatin hemicalcium trihydrate were dissolved in the mixture to form the spray solution. The solution was pumped into a "mini" spray-drying apparatus using the procedures outlined for Examples 1 and 2.

The thus-formed solid amorphous dispersion was analyzed by PXRD using the procedures outlined for Examples 1 and 2, and showed that both the torcetrapib and atorvastatin in the solid amorphous dispersion of Example 3 were almost completely amorphous.

An in vitro dissolution test was performed as described above. For this test, a sufficient amount of material was added to a microcentrifuge test tube so that the concentration of torcetrapib would have been 1000 μg/mL, if all of the drug had dissolved. This amount resulted in an atorvastatin concentration of 333 μgA/mL. The results are shown in Table 2.

Control 3

Control 3 consisted of a physical mixture of crystalline torcetrapib and atorvastatin hemicalcium trihydrate. For Control 3, 75 mg torcetrapib and 27.1 mg atorvastatin hemicalcium trihydrate were weighed into a scintillation vial and stirred with a spatula, resulting in the same drug ratio as the solid amorphous dispersion of Example 3. The mixture was blended 15 minutes with a Turbula blender. An in vitro dissolution tests was performed with Control 3 wherein a sufficient amount of material was added so that the concentration of torcetrapib would have been 1000 μg/mL, if all of the drug had dissolved. The total atorvastatin concentration would have been 333 μgA/mL for Control 3.

The concentrations of drug obtained in these samples were used to determine the maximum concentration of drug ("MDC$_{90}$") and the area under the concentration-versus-time curve ("AUC$_{90}$") during the initial ninety minutes. The results are shown in Table 2.

TABLE 2

| Sample | Torcetrapib Theoretical MDC (μgA/mL) | Torcetrapib MDC$_{90}$ (μgA/mL) | Torcetrapib AUC$_{90}$ (min * μgA/mL) | Atorvastatin Theoretical MDC (μgA/mL) | Atorvastatin MDC$_{90}$ (μgA/mL) | Atorvastatin AUC$_{90}$ (min * μgA/mL) |
|---|---|---|---|---|---|---|
| Example 3 (7.5/2.71/89.79 torcetrapib/ atorvastatin/ K$^+$HPMCAS-MG) | 1000 | 341 | 18,700 | 333 | 278 | 23,800 |
| Control 3 (73/27 torcetrapib/atorvastatin) | 1000 | <1 | <100 | 333 | 230 | 19,000 |

The results show that the solid amorphous dispersion of Example 3 provides concentration-enhancement of torcetrapib and atorvastatin, relative to a physical mixture of crystalline drugs alone. The solid amorphous dispersion of Example 3 provided a $MDC_{90}$ for torcetrapib that was greater than 341-fold that provided by crystalline drug, and an $AUC_{90}$ for torcetrapib that was greater than 187-fold that provided by crystalline drug. The solid amorphous dispersion of Example 3 also provided a $MDC_{90}$ for atorvastatin that was 1.2-fold that provided by crystalline drug, and an $AUC_{90}$ for atorvastatin that was 1.3-fold that provided by crystalline drug.

curve ("$AUC_{90}$") during the initial ninety minutes. The results are shown in Table 3.

TABLE 3

| Sample | Drug 1 Theoretical MDC (μgA/mL) | Drug 1 $MDC_{90}$ (μg/mL) | Drug 1 $AUC_{90}$ (min * μg/mL) | Atorvastatin Theoretical MDC (μgA/mL) | Atorvastatin $MDC_{90}$ (μgA/mL) | Atorvastatin $AUC_{90}$ (min * μgA/mL) |
|---|---|---|---|---|---|---|
| Example 4 (4.3/6.2/89.5 Drug 2/Atorvastatin/PVP) | 1000 | 895 | 54,500 | 1327 | 1282 | 98,800 |
| Control 4 (43/62 Drug 2/Atorvastatin) | 1000 | <1 | <200 | 1330 | 224 | 18,400 |

Example 4

A solid amorphous dispersion of [2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester ("Drug 2") and atorvastatin hemicalcium trihydrate was formed using the neutral polymer polyvinyl pyrrolidone (PVP; K-15; ISP Technologies, Inc.; Wayne, N.J.). The solid amorphous dispersion of contained 4.3 wt % Drug 2, 6.2 wt % atorvastatin hemicalcium trihydrate, and 89.5 wt % PVP. The solid amorphous dispersion of Example 4 was formed using a "mini" spray-drying apparatus using the procedures described for Examples 1 and 2.

The thus-formed solid amorphous dispersion was analyzed by PXRD using the procedures outlined for Examples 1 and 2, and showed that both Drug 2 and atorvastatin in the solid amorphous dispersion of Example 4 were almost completely amorphous.

An in vitro dissolution test was performed as described above. For this test, a sufficient amount of material was added to a microcentrifuge test tube so that the concentration of Drug 2 would have been 1000 μg/mL, if all of the drug had dissolved. This amount resulted in an atorvastatin concentration of 1327 μgA/mL. The results are shown in Table 3.

Control 4

Control 4 consisted of a physical mixture of crystalline Drug 2 and atorvastatin hemicalcium trihydrate. For Control 4, 43 mg Drug 2 and 61.8 mg atorvastatin hemicalcium trihydrate were weighed into a scintillation vial and stirred with a spatula, to obtain the same drug ratio as the solid amorphous dispersion of Example 4. The mixture was blended 15 minutes with a Turbula blender. A sufficient amount of material was added so that the concentration of Drug 2 would have been 1000 μg/mL, if all of the drug had dissolved. The total atorvastatin concentration would have been 1330 μgA/mL for Control 4.

The concentrations of drug obtained in these samples were used to determine the maximum concentration of drug ("$MDC_{90}$") and the area under the concentration-versus-time The results show that the solid amorphous dispersion of Example 4 provides concentration-enhancement of Drug 2 and atorvastatin, relative to a mixture of crystalline drugs alone. The solid amorphous dispersion of Example 4 provided a $MDC_{90}$ for Drug 2 that was greater than 895-fold that provided by crystalline drug, and an $AUC_{90}$ for Drug 2 that was greater than 270-fold that provided by crystalline drug. The solid amorphous dispersion of Example 4 also provided a $MDC_{90}$ for atorvastatin that was 5.7-fold that provided by crystalline drug, and an $AUC_{90}$ for atorvastatin that was 5.4-fold that provided by crystalline drug.

Example 5

A solid amorphous dispersion of torcetrapib and atorvastatin hemicalcium trihydrate was formed using the neutral polymer hydroxypropyl methyl cellulose (HPMC) and potassium carbonate. The solid amorphous dispersion of Example 5 contained 4.3 wt % torcetrapib, 6.2 wt % atorvastatin hemicalcium trihydrate, 87.5 wt % HPMC, and 2.0 wt % potassium carbonate. The solid amorphous dispersion of Example 5 was formed as follows. First, 875.2 mg of hydroxypropyl methyl cellulose (HPMC E3 Prem Methocel®, available from Dow Chemical Co., Midland, Mich.) was dissolved in water, and 43 mg torcetrapib, 61.8 mg of atorvastatin hemicalcium trihydrate, and 20 mg of potassium carbonate were dissolved in methanol. After the ingredients dissolved, the solutions were combined and stirred for 10 minutes, forming the spray solution. The solution was pumped into a "mini" spray-drying apparatus using the procedures outlined for Examples 1 and 2.

The thus-formed solid amorphous dispersion was analyzed by PXRD using the procedures outlined for Examples 1 and 2, and showed that both the torcetrapib and atorvastatin in the solid amorphous-dispersion of Example 5 were almost completely amorphous.

An in vitro dissolution test was performed as described above. For this test, a sufficient amount of material was added to a microcentrifuge test tube so that the concentration of torcetrapib would have been 1000 μg/mL, if all of the drug had dissolved. This amount resulted in an atorvastatin concentration of 1330 μgA/mL. The results are shown in Table 6.

Control 2

Control 2, described above, consisted of a physical mixture of crystalline torcetrapib and atorvastatin hem calcium trihydrate. A sufficient amount of material was added so that the concentration of torcetrapib would have been 1000 μg/mL, if all of the drug had dissolved. The total atorvastatin concentration would have been 1330 μgA/mL. The results for Control 2 dissolution (from Table 1) are shown again for comparison to Example 5.

The concentrations of drug obtained in these samples were used to determine the maximum concentration of drug ("$MDC_{90}$") and the area under the concentration-versus-time curve ("$AUC_{90}$") during the initial ninety minutes. The results are shown in Table 4.

TABLE 4

| Sample | Torcetrapib Theoretical MDC (μgA/mL) | Torcetrapib $MDC_{90}$ (μgA/mL) | Torcetrapib $AUC_{90}$ (min * μgA/mL) | Atorvastatin Theoretical MDC (μgA/mL) | Atorvastatin $MDC_{90}$ (μgA/mL) | Atorvastatin $AUC_{90}$ (min * μgA/mL) |
|---|---|---|---|---|---|---|
| Example 5 (4.3/6.2/87.5/2 torcetrapib/ atorvastatin/ HPMC/$K_2CO_3$) | 1000 | 1090 | 86,700 | 1330 | 794 | 53,900 |
| Control 2 (torcetrapib/ atorvastatin physical mixture) | 1000 | <1 | <100 | 1330 | 263 | 22,700 |

The results show that the solid amorphous dispersion of Example 5 provides concentration-enhancement of torcetrapib and atorvastatin, relative to a physical mixture of crystalline drugs alone. The solid amorphous dispersion of Example 5 provided a $MDC_{90}$ for torcetrapib that was greater than 1090-fold that provided by crystalline drug, and an $AUC_{90}$ for torcetrapib that was greater than 867-fold that provided by crystalline drug. The solid amorphous dispersion of Example 5 also provided a $MDC_{90}$ for atorvastatin that was 3.0-fold that provided by crystalline drug, and an $AUC_{90}$ for atorvastatin that was 2.4-fold that provided by crystalline drug.

Evaluation of Chemical Stability

The solid amorphous dispersions of Examples 1 to 5 were analyzed for degradation products formed during the spray-drying process. To analyze the samples by HPLC, a sample of the solid amorphous dispersion was dissolved in a solvent made by combining 150 mL 50 mM ammonium acetate (pH 7.0), 600 mL acetonitrile, and 250 mL methanol. The sample amount was adjusted so that the concentration of active atorvastatin in the solution was about 0.4 mgA/mL. The HPLC method utilized two mobile phases as follows. Mobile phase A was made by adding 3 mL acetic acid to 530 mL water and adjusting to pH 4.0 with ammonium hydroxide, then adding 270 mL acetonitrile and 200 mL tetrahydrofuran. Mobile phase B was made by adding 1 mL acetic acid to 100 mL water, adding half of the amount of ammonium hydroxide used to adjust Mobile phase A, then adding 700 mL acetonitrile and 200 mL tetrahydrofuran. The samples were analyzed using a Waters Spherisorb ODS2 column, with a solvent flow rate of 1.5 mL/min. Table 5 shows the solvent gradient used.

TABLE 5

| Time (min) | % A | % B |
|---|---|---|
| 0 | 100 | 0 |
| 15 | 100 | 0 |
| 35 | 0 | 100 |
| 50 | 0 | 100 |
| 51 | 100 | 0 |
| 60 | 100 | 0 |

The UV absorbance of atorvastatin and atorvastatin impurities were measured at a wavelength of 244 nm. The atorvastatin lactone impurity was chosen as the basis for comparison. All impurity peak areas were added and the lactone impurity as percent of total peak area was calculated to give the degree of degradation. The results are shown in Table 6.

Control 5

Control 5 (C5) consisted of a solid amorphous dispersion of torcetrapib and atorvastatin with the acidic polymer HPM-CAS-MG. The dispersion contained 20 wt % torcetrapib, 5 wt % atorvastatin hemicalcium trihydrate, and 75 wt % HPM-CAS-MG. First, a spray solution was formed containing 6 g torcetrapib, 1.5 g atorvastatin hemicalcium trihydrate, 22.5 g HPMCAS-MG (AQOAT-MG, available from Shin Etsu, Tokyo, Japan), and 570 g acetone. The spray solution was pumped using a high-pressure pump to a spray drier (a Niro type XP Portable Spray-Dryer with a Liquid-Feed Process Vessel ("PSD-1")), equipped with a pressure nozzle (Spraying Systems Pressure Nozzle and Body) (SK 79-16). The PSD-1 was equipped with a 9-inch chamber extension. The spray drier was also equipped with a diffuser plate having a 1% open area. The nozzle sat flush with the diffuser plate during operation. The spray solution was pumped to the spray drier at 109.5 g/min at a pressure of 150 psig. Drying gas (e.g., nitrogen) was directed through the diffuser plate at an inlet temperature of 100° C. The evaporated solvent and drying gas exited the spray drier at a temperature of 61.5° C. The resulting solid amorphous dispersion was collected in a cyclone. The solid amorphous dispersion formed using the above procedure was post-dried using a Gruenberg single-pass convection tray dryer operating at 30° C. The chemical stability was evaluated as indicated above and the results are shown in Table 6 for comparison.

TABLE 6

| Example | Atorvastatin Concentration in Dispersion (active, wt %) | Polymer | Degradant Concentration (% HPLC area) | Relative Degree of Improvement in Chemical Stability* |
|---|---|---|---|---|
| 1 | 3.2 | $K^+$CMEC | 0.95 | 5 |
| 2 | 13.1 | $K^+$CMEC | 0.94 | 5 |

TABLE 6-continued

| Example | Atorvastatin Concentration in Dispersion (active, wt %) | Polymer | Degradant Concentration (% HPLC area) | Relative Degree of Improvement in Chemical Stability* |
|---|---|---|---|---|
| 3 | 2.5 | K+HPMCAS-MG | 0.26 | 18 |
| 4 | 5.7 | PVP | <0.05 | >95 |
| 5 | 5.7 | HPMC | 0.12 | 40 |
| C5 | 4.6 | HPMCAS-MG | 4.75 | — |

*Degradant concentration for C5 divided by degradant concentration for the example.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A composition consisting of a solid amorphous dispersion, said dispersion consisting of
(1) a cholesteryl ester transfer protein (CETP) inhibitor,
(2) an acid sensitive HMG-CoA reductase inhibitor, and
(3) a concentration-enhancing polymer selected from the group consisting of neutral polymers, neutralized acidic polymers, and mixtures thereof;
wherein at least 60 wt % of each of said CETP inhibitor and said HMG-CoA reductase inhibitor in said dispersion is amorphous, and said dispersion has a relative degree of improvement in chemical stability of said HMG-CoA reductase inhibitor of at least about 1.1 relative to a control composition consisting essentially of a solid amorphous dispersion of said CETP inhibitor, said HMG-CoA reductase inhibitor, and the acidic polymer hydroxypropyl methyl cellulose acetate succinate, wherein at least a major portion of both said CETP inhibitor and said HMG-CoA reductase inhibitor in said control composition is amorphous.

2. The composition of claim 1 wherein at least 90 wt % of said HMG-CoA reductase inhibitor is amorphous.

3. The composition of claim 1 wherein at least 90 wt % of said CETP inhibitor is amorphous.

4. The composition of claim 1 wherein said CETP inhibitor in said dispersion is substantially homogeneous.

5. The composition of claim 1 wherein said dispersion has at least one glass-transition temperature intermediate that of a glass-transition temperature of said CETP Inhibitor and a glass-transition temperature of said concentration-enhancing polymer.

6. The composition of claim 1 further comprising a base.

7. The composition of claim 1 wherein said concentration-enhancing polymer is a neutral polymer selected from the group consisting of polyvinyl pyrrolidone, poloxamers, hydroxypropyl methyl cellulose acetate, hydroxypropyl methyl cellulose, hydroxypropyl cellulose, and hydroxyethyl cellulose acetate, and blends thereof.

8. The composition of claim 1 wherein said concentration-enhancing polymer is a neutralized form of an acidic polymer selected from the group consisting of hydroxypropyl methyl cellulose acetate succinate, hydroxypropyl methyl cellulose phthalate, cellulose acetate phthalate, cellulose acetate trimellitate, carboxymethyl ethyl cellulose, and blends thereof.

9. The composition of claim 1 wherein said CETP inhibitor is selected from the group consisting of [2R,4S]-4-[acetyl-(3,5-bis-trifluoromethyl-benzyl)-amino]-2-ethyl-6-trifluoromethyl-3,4-dihydro-2H-quinoline-1-carboxylic acid isopropyl ester (torcetrapib), [2R,4S]-4[(3,5-bis-trifluoromethyl-benzyl)-methoxycarbonyl-amino]-2-ethyl-6-trifluoromethyl-3,4-dihydro-2H-quinoline-1-carboxylic acid ethyl ester, [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester, and (2R)-3-[[3-(4-chloro-3-ethylphenoxy)phenyl][[3-(1,1,2,2-tetrafluoroethoxy)phenyl]methyl]amino]-1,1,1-trifluoro-2-propanol, (2R,4R,4aS)-4-[amino-(3,5-bis-(trifluoromethyl-phenyl)-methyl]-2-ethyl-6-(trifluoromethyl)-3,4-dihydroquinoline-1-carboxylic acid isopropyl ester, S-[2-([[1-(2-ethylbutyl)cyclohexyl]carbonyl]amino)phenyl]2-methylpropanethioate, trans-4-[[[2-[[[[3,5-bis(trifluoromethyl)phenyl]methyl](2-methyl-2H-tetrazol-5-yl)amino]methyl]-4-(trifluoromethyl)phenyl]ethylamino]methyl]-cyclohexaneacetic acid, and trans-4-[[[2-[[[[3,5-bis(trifluoromethyl)phenyl]methyl](2-methyl-2H-tetrazol-5-yl)amino]methyl]-5-methyl-4-(trifluoromethyl)phenyl]ethylamino]methyl]-cyclohexaneacetic acid.

* * * * *

UNITED STATES PATENT AND TRADEMARK OFFICE
CERTIFICATE OF CORRECTION

| | | |
|---|---|---|
| PATENT NO. | : 8,828,438 B2 | Page 1 of 1 |
| APPLICATION NO. | : 11/920473 | |
| DATED | : September 9, 2014 | |
| INVENTOR(S) | : Dwayne T. Friesen et al. | |

It is certified that error appears in the above-identified patent and that said Letters Patent is hereby corrected as shown below:

In the Specification:

Column 27, line 47, "oleoyi" should be --oleoyl--

Column 29, line 47, "2θ range of 40 to 30°" should be --2θ range of 4° to 30°--

Signed and Sealed this
Twenty-sixth Day of April, 2016

Michelle K. Lee
*Director of the United States Patent and Trademark Office*